United States Patent
Laserson

(10) Patent No.: US 10,706,545 B2
(45) Date of Patent: Jul. 7, 2020

(54) SYSTEMS AND METHODS FOR ANALYSIS OF ANATOMICAL IMAGES

(71) Applicant: Zebra Medical Vision Ltd., Shefayim (IL)

(72) Inventor: Jonathan Laserson, Tel Aviv (IL)

(73) Assignee: Zebra Medical Vision Ltd., Shefayim (IL)

( * ) Notice: Subject to any disclaimer, the term of this patent is extended or adjusted under 35 U.S.C. 154(b) by 159 days.

(21) Appl. No.: 15/972,912

(22) Filed: May 7, 2018

(65) Prior Publication Data

US 2019/0340763 A1 Nov. 7, 2019

(51) Int. Cl.
| | |
|---|---|
| *G06K 9/62* | (2006.01) |
| *A61B 6/00* | (2006.01) |
| *G06K 9/00* | (2006.01) |
| *G06T 7/00* | (2017.01) |

(52) U.S. Cl.
CPC ............ *G06T 7/0016* (2013.01); *A61B 6/502* (2013.01); *A61B 6/5235* (2013.01); *G06K 9/00456* (2013.01); *G06K 9/6221* (2013.01); *G06K 9/6256* (2013.01); *G06K 9/6267* (2013.01); *G06T 2207/10116* (2013.01); *G06T 2207/20081* (2013.01); *G06T 2207/30068* (2013.01)

(58) Field of Classification Search
None
See application file for complete search history.

(56) References Cited

U.S. PATENT DOCUMENTS

| | | |
|---|---|---|
| 5,857,030 A | 1/1999 | Gaborski et al. |
| 2006/0110021 A1 | 5/2006 | Luo et al. |
| 2013/0129165 A1 | 5/2013 | Dekel et al. |

(Continued)

FOREIGN PATENT DOCUMENTS

| | | |
|---|---|---|
| WO | WO 2018/015414 | 1/2018 |
| WO | WO 2019/215604 | 11/2019 |

(Continued)

OTHER PUBLICATIONS

International Search Report and the Written Opinion dated Sep. 8, 2019 From the International Searching Authority Re. Application No. PCT/IB2019/053725. (9 Pages).

(Continued)

*Primary Examiner* — Idowu O Osifade

(57) ABSTRACT

There is provided a method comprising: providing two anatomical images of a target individual, each captured at a unique orientation of the target individual, inputting first and second anatomical images respectively into a first and second convolutional neural network (CNN) of a classifier to respectively output first and second feature vectors, inputting a concatenation of the first and second feature vectors into a fully connected layer of the classifier, and computing an indication of distinct visual finding(s) present in the anatomical images by the fully connected layer, wherein the statistical classifier is trained on a training dataset including two anatomical images of each respective sample individual, each image captured at a respective unique orientation of the target individual, and a tag created based on an analysis that maps respective individual sentences of a text based radiology report to one of multiple indications of visual findings.

22 Claims, 16 Drawing Sheets

(56) References Cited

U.S. PATENT DOCUMENTS

| | | | |
|---|---|---|---|
| 2017/0221204 A1 | 8/2017 | Shinagawa | |
| 2018/0101645 A1 | 4/2018 | Sorenson et al. | |
| 2018/0259608 A1* | 9/2018 | Golden | G06N 3/084 |
| 2019/0340752 A1 | 11/2019 | Brestel et al. | |
| 2019/0340753 A1 | 11/2019 | Brestel et al. | |

FOREIGN PATENT DOCUMENTS

| | | |
|---|---|---|
| WO | WO 2019/215605 | 11/2019 |
| WO | WO 2019/215606 | 11/2019 |

OTHER PUBLICATIONS

International Search Report and the Written Opinion dated Sep. 12, 2019 From the International Searching Authority Re. Application No. PCT/IB2019/053724. (12 Pages).

Dong et al. "Learning to Read Chest X-Ray Images From 16000+ Examples Using CNN", 2017 Proceedings of the IEEE/ACM International Conference on Connected Health: Applications, Systems and Engineering Technologies, CHASE, Philadelphia, PA, USA, Jul. 17-19, 2017, p. 51-57, Jul. 17, 2017.

Kamnitsas et al. "Efficient Multi-Scale 3D CNN With Fully Connected CRF for Accurate Brain Lesion Segmentation", Medical Image Analysis, 36: 61-78, Available Online Oct. 29, 2016.

Mayer et al. "Transfer Learning for Data Triage Applications", IS&T International Symposium on Electronic Imaging 2018, Visual Information Processing and Communication IX, p. 175-1-175-6, Jan. 1, 2018.

Taylor et al. "Automated Detection of Moderate and Large Pneumothorax on Frontal Chest X-rays Using Deep Convolutional Neural Networks: A Retrospective Study", PLoS Medicine, 15(11): e1002697, pp. 1-15, Nov. 20, 2018.

International Search Report and the Written Opinion dated Sep. 25, 2019 From the International Searching Authority Re. Application No. PCT/IB2019/053726. (11 Pages).

European Search Report and the European Search Opinion dated Sep. 26, 2019 From the European Patent Office Re. Application No. 19173136.3. (8 Pages).

De Vos et al. "ConvNet-Based Localization of Anatomical Structures in 3D Medical Images", ARXIV.Org, Cornell University Library, XP080763925, ArXiv:1704.05629v1, p. 1-12, Apr. 19, 2017.

Brady et al. "Discrepancy and Error in Radiology: Concepts, Causes and Consequences", The Ulster Medical Journal, 81(1): 3-9, Jan. 2012.

Bruno et al. "Understanding and Confronting Our Mistakes: The Epidemiology of Error in Radiology and Strategies for Error Reduction", RadioGraphics, 35(6): 1668-1676, Published Online Oct. 14, 2015.

Demner-Fushman et al. "Annotation of Chest Radiology Reports for Indexing and Retrieval", Proceedings of the First International Workshop on Multimodal Retrieval in the Medical Domain, MRDM '15, Vienna, Austria, Mar. 29, 2015, LNCS 9059: 99-111, Mar. 29, 2015.

Hanna et al. "Effect of Shift, Schedule, and Volume on Interpretice Accuracy: A Retrospective Analysis of 2.9 Million Radiologic Examinations", Radiology, 287(1): 205-212, Published Online Nov. 20, 2017.

Huang et al. "Densely Connected Convolutional Networks", Proceedings of the IEEE Conference on Computer Vision and Pattern Recognition, CVPR '17, Honolulu, Hawaii, USA, Jul. 21-26, 2017, p. 4700-4708, Jul. 21, 2017.

Jing et al. "On the Automatic Generation of Medical Imaging Reports", arXiv:1711.08195v1, p. 1-9, Nov. 22, 2017.

Rajpurkar et al. "CheXNet: Radiologist-Level Pneumonia Detection on Chest X- Rays With Deep Learning", arXiv:1711.05225v1, 7 P., Nov. 14, 2017.

Robinson et al. "Variation Between Experienced Observers in the Interpretation of Accident and Emergency Radiographs", The British Journal of Radiology, 72: (856): 323-330, Apr. 1999.

Shin et al. "Learning to Read Chest X-Rays: Recurrent Neural Cascade Model for Automated Image Annotation", Proceedings of the IEEE Conference of Computer Vision and Pattern Recognition, CVPR '16, Las Vegas, NV, USA, Jun. 27-30, 2016, p. 2497-2506, Jun. 27, 2016.

Wang et al. "ChestX-Ray8: Hospital-Scale Chest X-Ray Database and Benchmarks on Weakly-Supervised Classification and Localization of Common Thorax Diseases", Proceedings of the IEEE Conference on Computer Vision and Pattern Recognition, CVPR '17, honolulu, Hawaii, USA, Jul. 21-26, 2017, p. 2097-2106, Jul. 21, 2017.

\* cited by examiner

| # | finding | total | % | # | finding | total | % |
|---|---|---|---|---|---|---|---|
| 1 | abnormal aorta | 15,932 | 1.66 | 21 | mass | 633 | 0.07 |
| 2 | aortic calcification | 11,508 | 1.20 | 22 | mediastinal widening | 1,639 | 0.17 |
| 3 | artificial valve | 5,847 | 0.61 | 23 | much bowel gas | 441 | 0.05 |
| 4 | atelectasis | 5,492 | 0.57 | 24 | nodule | 553 | 0.06 |
| 5 | bronchial wall thickening | 2,773 | 0.29 | 25 | orthopedic surgery | 717 | 0.07 |
| 6 | cardiac pacer | 17,378 | 1.81 | 26 | osteopenia | 5,585 | 0.58 |
| 7 | cardiomegaly | 95,137 | 9.92 | 27 | pleural effusion | 16,688 | 1.74 |
| 8 | central line | 3,802 | 0.40 | 28 | pleural thickening | 8,164 | 0.85 |
| 9 | consolidation | 34,260 | 3.57 | 29 | pneumothorax | 741 | 0.08 |
| 10 | costophrenic angle blunting | 13,673 | 1.43 | 30 | pulmonary edema | 8,637 | 0.90 |
| 11 | degenerative changes | 18,545 | 1.93 | 31 | rib fracture | 4,607 | 0.48 |
| 12 | elevated diaphragm | 21,913 | 2.28 | 32 | scoliosis | 4,907 | 0.51 |
| 13 | fibrotic changes | 11,027 | 1.15 | 33 | soft tissue calcifications | 1,086 | 0.11 |
| 14 | fracture | 526 | 0.05 | 34 | sternotomy wires | 45,002 | 4.69 |
| 15 | granuloma | 1,475 | 0.15 | 35 | surgical clips noted | 8,147 | 0.85 |
| 16 | hernia diaphragm | 8,892 | 0.93 | 36 | thickening of fissure | 1,714 | 0.18 |
| 17 | hilar prominence | 10,407 | 1.08 | 37 | trachea deviation | 601 | 0.06 |
| 18 | hyperinflation | 37,319 | 3.89 | 38 | transplant | 5,180 | 0.54 |
| 19 | interstitial markings | 97,703 | 10.18 | 39 | tube | 2,025 | 0.21 |
| 20 | kyphosis | 5,531 | 0.58 | 40 | vertebral height loss | 1,212 | 0.13 |

FIG. 7

| finding | pool pos | pool neg | avg. agreement w/ rads report | avg. agreement w/ rads avg. rad | avg. agreement w/ rads textray | $\Delta$ (CI) textray vs. rads |
|---|---|---|---|---|---|---|
| pulmonary edema | 128 | 482 | 0.613 | 0.639 | 0.730 | +0.09 (0.07, 0.11) |
| elevated diaphragm | 202 | 77 | 0.731 | 0.675 | 0.754 | +0.08 (0.05, 0.10) |
| abnormal aorta | 198 | 80 | 0.736 | 0.693 | 0.771 | +0.08 (0.05, 0.11) |
| hyperinflation | 95 | 80 | 0.678 | 0.619 | 0.657 | +0.04 (-0.02, 0.10) |
| vertebral height loss | 126 | 55 | 0.781 | 0.742 | 0.757 | +0.02 (-0.02, 0.06) |
| atelectasis | 201 | 78 | 0.778 | 0.756 | 0.767 | +0.01 (-0.03, 0.04) |
| cardiomegaly | 238 | 372 | 0.755 | 0.861 | 0.866 | +0.01 (-0.02, 0.03) |
| pleural effusion | 207 | 73 | 0.905 | 0.893 | 0.896 | +0.00 (-0.02, 0.03) |
| consolidation | 194 | 78 | 0.690 | 0.730 | 0.707 | -0.02 (-0.07, 0.02) |
| pneumothorax | 111 | 124 | 0.830 | 0.855 | 0.823 | -0.03 (-0.08, 0.01) |
| rib fracture | 183 | 76 | 0.683 | 0.799 | 0.745 | -0.05 (-0.10, -0.01) |
| hilar prominence | 184 | 426 | 0.552 | 0.797 | 0.736 | -0.06 (-0.09, -0.03) |

FIG. 8

| finding | % pos studies included | | % pos findings correctly labeled | |
|---|---|---|---|---|
| | fully-covered | any-hit | fully-covered | any-hit |
| abnormal aorta | 44.9 | 81.8 | 97.8 | 87.7 |
| atelectasis | 13.9 | 64.2 | 78.6 | 47.3 |
| cardiomegaly | 55.0 | 95.0 | 100.0 | 99.1 |
| elevated diaphragm | 42.1 | 76.7 | 95.3 | 81.9 |
| hilar prominence | 43.5 | 84.2 | 96.2 | 86.5 |
| hyperinflation | 56.8 | 85.3 | 90.7 | 91.4 |
| consolidation | 24.2 | 50.5 | 87.2 | 58.2 |
| pleural effusion | 34.3 | 80.7 | 94.4 | 70.1 |
| pneumothorax | 19.8 | 56.8 | 50.0 | 39.7 |
| pulmonary edema | 57.0 | 93.8 | 86.3 | 75.0 |
| rib fracture | 34.4 | 63.4 | 82.5 | 61.2 |
| vertebral height loss | 20.6 | 64.3 | 73.1 | 39.5 |

FIG. 9

| # | finding | base | PA | FC | # | finding (cont.) | base | PA | FC |
|---|---|---|---|---|---|---|---|---|---|
| 1 | abnormal aorta | 0.902 | 0.898 | 0.887 | 21 | mass | 0.941 | 0.937 | 0.894 |
| 2 | aortic calcification | 0.945 | 0.935 | 0.930 | 22 | mediastinal widening | 0.909 | 0.904 | 0.885 |
| 3 | artificial valve | 0.994 | 0.986 | 0.989 | 23 | increased bowel gas | 0.917 | 0.895 | 0.867 |
| 4 | atelectasis | 0.884 | 0.898 | 0.877 | 24 | nodule | 0.845 | 0.852 | 0.882 |
| 5 | bronchial wall thick | 0.852 | 0.849 | 0.852 | 25 | orthopedic surgery | 0.856 | 0.849 | 0.817 |
| 6 | cardiac pacer | 0.998 | 0.997 | 0.997 | 26 | osteopenia | 0.888 | 0.873 | 0.846 |
| 7 | cardiomegaly | 0.928 | 0.930 | 0.918 | 27 | pleural effusion | 0.957 | 0.959 | 0.949 |
| 8 | central line | 0.996 | 0.992 | 0.990 | 28 | pleural thickening | 0.816 | 0.811 | 0.811 |
| 9 | consolidation | 0.838 | 0.818 | 0.838 | 29 | pneumothorax | 0.929 | 0.935 | 0.910 |
| 10 | costoph. angle blunt. | 0.917 | 0.919 | 0.896 | 30 | pulmonary edema | 0.943 | 0.945 | 0.944 |
| 11 | degenerative changes | 0.835 | 0.834 | 0.812 | 31 | rib fracture | 0.883 | 0.862 | 0.855 |
| 12 | elevated diaphragm | 0.919 | 0.919 | 0.908 | 32 | scoliosis | 0.852 | 0.843 | 0.824 |
| 13 | fibrotic changes | 0.858 | 0.861 | 0.839 | 33 | soft tissue calc. | 0.709 | 0.715 | 0.703 |
| 14 | fracture | 0.718 | 0.735 | 0.616 | 34 | sternotomy wires | 0.989 | 0.986 | 0.988 |
| 15 | granuloma | 0.727 | 0.745 | 0.689 | 35 | surgical clips noted | 0.905 | 0.884 | 0.883 |
| 16 | hernia diaphragm | 0.986 | 0.988 | 0.984 | 36 | thickening of fissure | 0.892 | 0.875 | 0.870 |
| 17 | hilar prominence | 0.884 | 0.880 | 0.855 | 37 | trachea deviation | 0.943 | 0.918 | 0.908 |
| 18 | hyperinflation | 0.839 | 0.838 | 0.844 | 38 | transplant | 0.999 | 0.999 | 0.989 |
| 19 | interstitial markings | 0.776 | 0.779 | 0.781 | 39 | tube | 0.940 | 0.940 | 0.911 |
| 20 | kyphosis | 0.941 | 0.907 | 0.925 | 40 | vertebral height loss | 0.809 | 0.773 | 0.766 |

FIG. 12

| sentence | #reports | sentence | #reports |
|---|---|---|---|
| The heart is enlarged | 39,245 | Twisted aorta | 6,771 |
| The heart is widened | 20,270 | Infiltrate | 6,540 |
| Enlarged heart | 14,689 | Increased lung volume | 6,494 |
| Chronic bronchial changes | 9,515 | After sternotomy | 6,268 |
| Enhanced interstitial markings in the lungs | 9,216 | Interstitial changes in the lungs | 5,303 |
| Permanent cardiac pacer | 6,881 | Hyperinflation | 5,064 |

FIG. 14

| finding | AAR of each radiologist | | | | | | | rad. average |
|---|---|---|---|---|---|---|---|---|
| | A | B | C | D | E | F | G | |
| abnormal aorta | 0.75 | 0.72 | | | 0.6 | | | 0.69 |
| atelectasis | | | | 0.77 | | 0.73 | 0.77 | 0.76 |
| cardiomegaly | | | 0.85 | 0.86 | | | 0.87 | 0.86 |
| elevated diaphragm | | | | 0.67 | 0.6 | 0.75 | | 0.68 |
| hilar prominence | | | | 0.79 | 0.79 | | 0.82 | 0.80 |
| hyperinflation | 0.65 | | | | 0.69 | 0.52 | | 0.62 |
| consolidation | 0.77 | | 0.72 | 0.7 | | | | 0.73 |
| pleural effusion | 0.91 | | | 0.88 | 0.9 | | | 0.89 |
| pneumothorax | | | | 0.87 | 0.84 | 0.85 | | 0.86 |
| pulmonary edema | | | 0.71 | 0.61 | | | 0.6 | 0.64 |
| rib fracture | | | | 0.8 | 0.79 | 0.81 | | 0.80 |
| vertebral height loss | 0.75 | 0.8 | | | | 0.68 | | 0.74 |

FIG. 16

SYSTEMS AND METHODS FOR ANALYSIS OF ANATOMICAL IMAGES

BACKGROUND

The present invention, in some embodiments thereof, relates to medical anatomical images and, more specifically, but not exclusively, to systems and methods for automated analysis of medical anatomical images.

Manual visual assessment (e.g., by a radiologist) of medical anatomical images, such as x-ray images, is a challenging and time consuming task due to the large amount of information that needs to be processed. The radiologist looks to identify relevant features of the anatomical images when a large number of possible features are possible. For example, each medical anatomical image includes multiple anatomical objects, such as bones, different organs, and different connective tissues, each of which may present with different findings.

SUMMARY

According to a first aspect, a computer implemented method for identification of an indication of at least one of a plurality of visual findings in at least one of two anatomical images of a target individual, comprises: providing two anatomical images of a body portion of a target individual, each of the two anatomical images captured at a unique orientation of at least the body portion of the target individual, inputting a first anatomical image of the two anatomical images into a first convolutional neural network (CNN) of a statistical classifier to output a first feature vector, inputting a second anatomical image of the two anatomical images into a second CNN of the statistical classifier to output a second feature vector, inputting a concatenation of the first feature vector and the second feature vector into a fully connected layer of the statistical classifier, and computing an indication of at least one of a plurality of distinct visual findings present in at least one of the two anatomical images by the fully connected layer, wherein the statistical classifier is trained on a training dataset including, or each of a plurality of sample individuals, two anatomical images of a body portion of the respective sample individual each captured at a respective unique orientation of at least the body portion of the target individual, and a tag associated with the two anatomical images, wherein the tag is created based on an analysis that maps respective individual sentences of a text based radiology report to one of a plurality of indications of visual findings.

According to a second aspect, a method of training a statistical classifier for identification of at least one of a plurality of visual findings in at least one of two anatomical images of a target individual, comprises: providing, for each of a plurality of sample individuals, two anatomical images of a body portion of the respective sample individual each captured at a respective unique orientation of at least the body portion of the target individual, and a text based radiology report including a plurality of sentences, creating, for each of the plurality of sample individuals, a respective tag according to an analysis that maps at least one of the plurality of sentences to a respective certain indication of a plurality of indications of distinct visual findings present in at least one of the two anatomical images of the respective individual, and training a statistical classifier for identification of at least one of a plurality of visual findings in at least one of two anatomical images of the body portion of a target individual according to a training dataset comprising the respective two anatomical images and respective tag for each of the plurality of sample individual.

According to a third aspect, a system for identification of an indication of at least one of a plurality of visual findings in at least one of two anatomical images of a target individual, comprises: a non-transitory memory having stored thereon a code for execution by at least one hardware processor, the code comprises: code for providing two anatomical images of a body portion of a target individual, each of the two anatomical images captured at a unique orientation of at least the body portion of the target individual, code for inputting a first anatomical image of the two anatomical images into a first convolutional neural network (CNN) of a statistical classifier to output a first feature vector, code for inputting a second anatomical image of the two anatomical images into a second CNN of the statistical classifier to output a second feature vector, code for inputting a concatenation of the first feature vector and the second feature vector into a fully connected layer of the statistical classifier, and code for computing an indication of at least one of a plurality of distinct visual findings present in at least one of the two anatomical images by the fully connected layer, wherein the statistical classifier is trained on a training dataset including, or each of a plurality of sample individuals, two anatomical images of a body portion of the respective sample individual each captured at a respective unique orientation of at least the body portion of the target individual, and a tag associated with the two anatomical images, wherein the tag is created based on an analysis that maps respective individual sentences of a text based radiology report to one of a plurality of indications of visual findings.

At least some of the systems, methods, apparatus, and/or code instructions described herein address the technical problem of automatically identifying visual findings in anatomical images. Automatic detection of visual findings in anatomical images is a challenging technical problem due to several reasons, for example, the large number of possible visual findings that may be found in anatomical images, the large number of possible combinations of visual findings that may be found in anatomical images, lack of visual clarity in identifying certain visual findings (even amongst human interpreters). For example, as described herein with reference to one implementation, any combination of 40 possible visual findings may be identified by the trained classifier. Is it noted that some combination of visual findings appear together in certain medical conditions, for example, cardiomegaly, hilar prominence, and pulmonary edema, which may be found together in the setting of congestive heart failure.

At least some of the systems, methods, apparatus, and/or code instructions described herein improve the technical field of automated analysis of anatomical images to identify visual findings. One exemplary improvement is based on the use of existing radiology reports associated with existing anatomical images (e.g., stored in PACS servers and/or EMR servers), as described herein, which allows to create very large training datasets using existing data, without requiring manual labeling of the anatomical images. As described herein, the labels are automatically generated based on the pre-created text based radiology reports associated with the anatomical images. The ability to use very large datasets improves the accuracy of the trained classifier(s). Another exemplary improvement is based on the use of two or more anatomical images captured of the patient at different orientation angles. The processing of the two or more images by the classifier increased the accuracy of classification, since for example, certain visual findings are better detected at a certain orientation and/or certain visual findings are better detected when both (or more) images are analyzed.

At least some of the systems, methods, apparatus, and/or code instructions described herein improve the performance of a computing device that executes code instructions that implement the classifier for automatically detecting visual finding(s) in two or more anatomical images. The improvement in performance may be based on an increase in accuracy of detecting the visual findings, and/or ability to detect any combination of one or more visual findings for a set of possible visual findings, using existing computing resources (e.g., processor(s), and/or data storage). For example, the trained classifier may detect visual findings with increased sensitivity in comparison to other automated methods and/or in comparison to human ability. In another example, the improvement in performance of the computing device's ability to accurately detect visual findings depicted in the anatomical images is based on training the classifier according to the visual findings rather than, for example, training the classifier for detection of clinical interpretation and/or diagnosis. The classifier provides the user with identified visual findings, which are more objective findings, in comparison to clinical interpretation and/or diagnosis which tend to be more subjective.

In a further implementation form of the first, second, and third aspects, the two anatomical images depict non-parallel viewing planes of the patient from the anatomical imaging sensor.

In a further implementation form of the first, second, and third aspects, each one of the plurality of indications of distinct visual findings is based on one of a plurality of clusters created by clustering a plurality of sentences from respective text based radiology reports of a plurality of sample individuals.

In a further implementation form of the first, second, and third aspects, the anatomical imaging device comprises an x-ray machine that captures a two dimensional anatomical image.

In a further implementation form of the first, second, and third aspects, the anatomical imaging device comprises a mammography machine that captures a two dimensional anatomical images of two views per breast, including a mediolateral oblique (MLO) view and a craniocaudal (CC) view In a further implementation form of the first, second, and third aspects, a first anatomical image is captured when the target individual is oriented laterally relative to an anatomical imaging device, and a second anatomical image is captured when the target individual is oriented anterior-posterior (AP) or posterior-anterior (PA) relative to the anatomical imaging device.

In a further implementation form of the first, second, and third aspects, a first anatomical image is captured when the target individual is oriented supine relative to an anatomical imaging device, and a second anatomical image is captured when the target individual is oriented upright relative to the anatomical imaging device.

In a further implementation form of the first, second, and third aspects, the body portion of the target individual comprises at least one of: a chest, an abdomen, and a limb of the target individual.

In a further implementation form of the first, second, and third aspects, the classifier computers the indication of at least two visual findings in at least one of the two anatomical images by the fully connected layer.

In a further implementation form of the first, second, and third aspects, the plurality of visual findings include at least two members selected from the group consisting of: abnormal aorta, aortic calcification, artificial valve, atelectasis, bronchial wall thickening, cardiac pacer, cardiomegaly, central line, consolidation, costrophrenic angle blunting, degenerative changes, elevated diaphragm, fracture, granuloma, hernia diaphragm, hilar prominence, hyperinflation, interstitial markings, kyphosis, mass, mediastinal widening, much bowel gas, nodule, orthopedic surgery, osteopenia, pleural effusion, pleural thickening, pneumothorax, pulmonary edema, rib fracture, scoliosis, soft tissue calcification, sternotomy wires, surgical clip noted, thickening of fissure, trachea deviation, transplant, tube, and vertebral height loss.

In a further implementation form of the first, second, and third aspects, the plurality of visual findings include at least two members selected from the group consisting of: masses, calcifications, calcified masses, calcification clusters, distortions, asymmetries, densities and scars.

In a further implementation form of the first, second, and third aspects, the method and/or the system further comprise computing by the statistical classifier, a confidence score indicative of a probability of the presence of each of the plurality of visual findings in at least one of the two anatomical images.

In a further implementation form of the first, second, and third aspects, the method and/or the system further comprise computing a heat map according to the confidence score for each of the plurality of visual findings, and presenting the heat map as an overlay of at least one of the two anatomical images.

In a further implementation form of the first, second, and third aspects, the method and/or the system further comprise clustering the plurality of sentences from the respective text based radiology report of the plurality of sample individuals into a plurality of clusters, wherein each one of the plurality of indications of distinct visual findings is based on one of the plurality of clusters.

In a further implementation form of the second aspect, the statistical classifier includes a first CNN that computes a first feature vector according to an inputted first anatomical image of the two anatomical images, a second CNN designed to output a second feature vector according to an inputted second anatomical image of the two anatomical images, and a fully connected layer that outputs an indication of at least one of a plurality of visual findings according to a concatenation of the first feature vector and the second feature vector.

In a further implementation form of the first, second, and third aspects, for each text based radiology report of each of the plurality of sample individuals, a sub-set of the plurality of sentences of the respective text based radiology report indicative of positive findings are mapped to the one of the plurality of indications of visual findings, and another sub-set of the plurality of sentences indicative of at least one of negative findings, neutral data, and ambiguous data is indicative of no visual findings and not mapped to one of the plurality of indications of visual findings.

In a further implementation form of the first, second, and third aspects, the method and/or the system further comprise creating a fully covered training dataset according to a sub-set of the text based radiology reports of the plurality of sample individuals, where for respective text based radiology report of each of the sub-set of the text based radiology reports, each one of the sentences of the respective text based radiology report is mapped to one of: one of the plurality of indications of visual findings, a negative finding, and neutral data, wherein the classifier is trained according to the fully covered training dataset.

In a further implementation form of the first, second, and third aspects, the method and/or the system further comprise creating an any hit training dataset according to a sub-set of the text based radiology reports of the plurality of sample individuals, where for respective text based radiology report of each of the sub-set of the text based radiology reports, at least one of the sentences of the respective text based radiology report is mapped to one of the plurality of indications of visual findings, wherein the classifier is trained according to the any hit training dataset.

In a further implementation form of the first, second, and third aspects, the statistical classifier is trained according to a main loss function based on a mean of binary cross-entropy losses.

In a further implementation form of the third aspect, the system further comprises code for training a statistical classifier for identification of at least one of a plurality of visual findings in at least one of two anatomical images of a target individual, comprising: code for providing, for each of a plurality of sample individuals, two anatomical images of a body portion of the respective sample individual each captured at a respective unique orientation of at least the body portion of the target individual, and a text based radiology report including a plurality of sentences, code for creating, for each of the plurality of sample individuals, a respective tag according to an analysis that maps at least one of the plurality of sentences to a respective certain indication of a plurality of indications of distinct visual findings present in at least one of the two anatomical images of the respective individual, and code for training a statistical classifier for identification of at least one of a plurality of visual findings in at least one of two anatomical images of the body portion of a target individual according to a training dataset comprising the respective two anatomical images and respective tag for each of the plurality of sample individual.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 7 is a table of the top 40 visual findings identified from the radiology reports associated with the training images used in an experiment, in accordance with some embodiments of the present invention;

FIG. 8 is a table summarizing the composition of evaluation sets used in an experiment, in accordance with some embodiments of the present invention; and FIG. 9 is a table summarizing the percent of positive studies that include 12 visual findings of the evaluation set used in the experiment, and the percent of the positive studies that had correct label assignments, in accordance with some embodiments of the present invention;

FIG. 10 includes multiple ROC plots of the trained classifier for each of the 40 visual findings of chest x-ray findings described in the experiment, in accordance with some embodiments of the present invention;

FIG. 12 is a table presenting results of a variant of the classifier described herein trained only with one anatomical image (i.e., PA view) for comparison with the classifier described herein trained with two anatomical images (i.e., denoted base, trained using PA and lateral views) used in the experiments, in accordance with some embodiments of the present invention;

FIG. 14 is a table presenting the most frequent positive sentences and corresponding number of occurrences in the set of radiology reports used in the experiment, in accordance with some embodiments of the present invention;

FIG. 16 is a table presenting agreement rates of assigned manual radiology taggers (marked as A-G) for different visual findings, as described with reference to the experiment.

DETAILED DESCRIPTION

Figure 1:
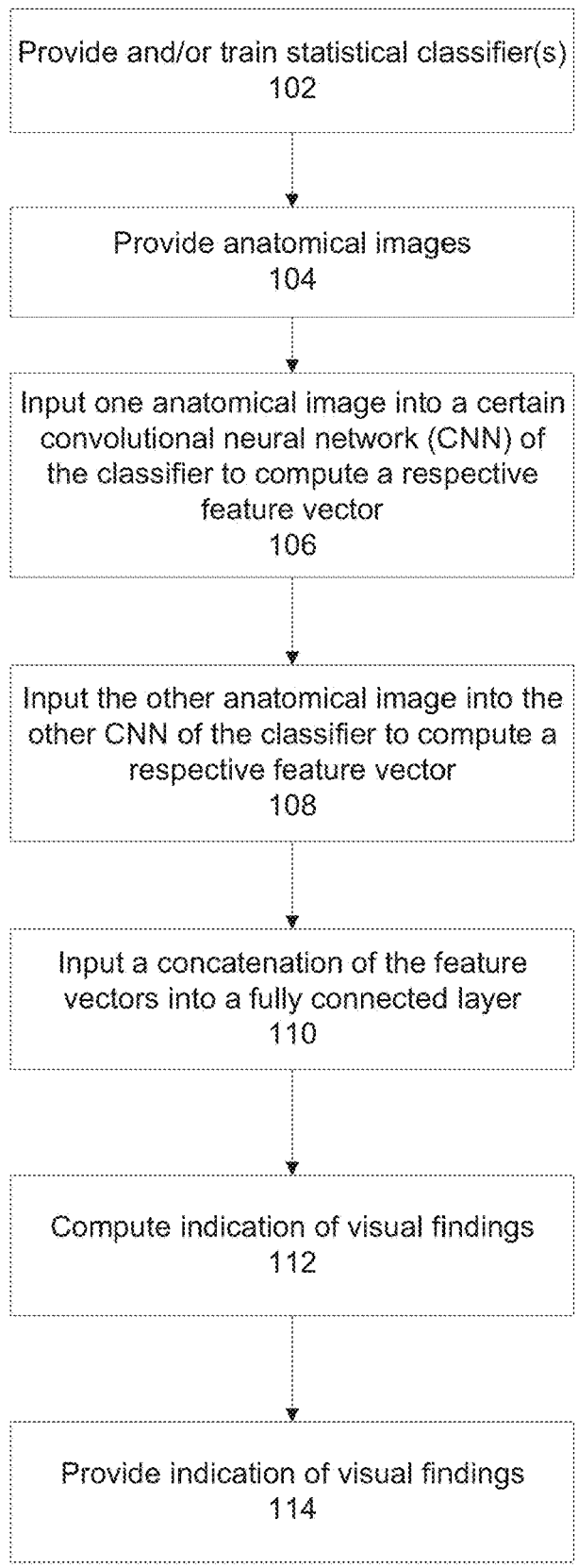
FIG. 1 is a flowchart of a method for identification of one or more visual findings of multiple possible visual findings in at least one of two anatomical images of a target individual, in accordance with some embodiments of the present invention.

The present invention, in some embodiments thereof, relates to medical anatomical images and, more specifically, but not exclusively, to systems and methods for automated analysis of medical anatomical images.

As used herein, the term two anatomical images is exemplary and not necessarily limiting. Two anatomical images represent the most common medical practice, for example, two associated anatomical images and their text based radiology report may be stored in existing PACS and/or EMRs. It is noted that a larger number of anatomical images may be implemented based on the teachings described herein. For example, a classifier may be trained to analyze three anatomical images using respective CNNs trained for each of the three types of anatomical images. Such classifier may be used, for example, to analyze the shoulder when multiple anatomical images at different views are obtained, for example, AP neural views, internal rotation, external rotation, lateral view, and glenoid view.

As used herein, the term unique orientation of at least the body portion of the patient, or unique patient orientation refers to each of the two anatomical images being captured at different orientations of the body portion of the patient and/or of the whole body of the patient, for example, rotation of the patient relative to the imaging sensor such as a front view and a side view, breast mediolateral oblique (MLO) view and craniocaudal view, changing position from lying down to standing up, and rotation of a limb from a first position to a second position, for example, an internal rotation of the leg or arm and an external rotation of the leg or arm. The anatomical images are captured at a unique sensor angle between an anatomical imaging sensor (also referred to herein as an anatomical imaging device) that captured the image(s) and a respective orientation of the body portion of the target individual. The unique viewing angle may have, for example, an oblique angle, or a right angle, or other non-parallel value. The two anatomical images do not represent viewing planes that are parallel to one another, for example, the two anatomical images are not parallel slices of a 3D CT scan. The two anatomical images may be captured by rotation of the patient relative to the imaging sensor, rather than simply adjusting the distance from the patient to the imaging sensor. Alternatively, the two anatomical images may be captured by a rotation and/or repositioning of the imaging sensor relative to the patient, for example, moving the imaging device to the front or side of the patient, rather than simply translating the imaging sensor towards or away from the patient. It is noted that the two anatomical images may be extracted as 2D slices from 3D data when the 2D slices are non-parallel planes, for example, oblique slices or slices at right angles to one another extracted from imaging data collected by an MRI machine. Examples of two anatomical images captured at respective unique patient orientations include: anterior-posterior (AP) and lateral views for chest x-rays, posterior-anterior (PA) and lateral views for chest x-rays, two views of the abdomen for abdominal x-rays, and two views, for example, a supine view and an upright view. In another example, the two or more anatomical images may include mammographic images of one or both breasts, for example breast mediolateral oblique (MLO) view and craniocaudal view. Exemplary visual findings for the two or more mammographic views include: masses, calcifications, calcified masses, calcification clusters, distortions, asymmetries, densities and scars, and other visual findings commonly described by radiologists in radiological reports.

An aspect of some embodiments of the present invention relates to systems, an apparatus, methods, and/or code instructions (i.e., stored by a data storage device, executable by one or more hardware processors) for identification of one or more visual findings of multiple possible visual findings in at least one of two anatomical images. Each of the two anatomical images is captured at a unique orientation of at least the body portion of the target individual. One of the anatomical images, which depicts one of the unique orientations, is fed into a convolutional neural network (CNN) of a statistical classifier. The CNN is designed to process anatomical images depicting the certain unique orientation. The other anatomical image, which depicts another of the unique orientations, is fed into another CNN of the statistical classifier. The other CNN is designed to process anatomical images depicting the other unique orientation. Each CNN outputs a respective feature vector. The two outputted feature vectors are concatenated and inputted into a fully connected layer. The fully connected layer outputs an indication of one or more distinct visual findings present in one or both of the anatomical images. The indication(s) are according to a set of possible distinct visual findings that may be found in one or both of the anatomical images.

The anatomical images represent a bag of findings, where each anatomical image may represent no visual findings, one visual finding, or multiple visual findings, up to the maximum total number of distinct visual findings. The classifier described herein detects one or more visual findings from a set of possible visual findings, for example, in contrast to other methods in which a classifier is trained to detect a single type of feature in an anatomical image.

An aspect of some embodiments of the present invention relates to systems, an apparatus, methods, and/or code instructions (i.e., stored by a data storage device, executable by one or more hardware processors) for training a statistical classifier for identification one or more visual findings from multiple possible visual findings in a set of two anatomical images of a target individual. The statistical classifier is trained according to a training dataset created based on two anatomical images provided for each sample individual of multiple sample individuals. The two anatomical images are captured at respective unique orientation of at least the body portion of the target individual. Each set of two anatomical images is associated with a text based radiology report (e.g., created by a radiologist manually interpreting the images). Each text based radiology report includes multiple sentences. One or more of the sentences map to one of possible distinct visual findings present in one or both of the anatomical images of the respective sample individual.

The set of possible distinct visual findings represent a global set of indications. Different sentences from different radiology reports may map to the same visual finding. The variations in sentences arise from personalized wording used by the radiologist, which effectively all of the variations of the sentences actually refer to the same type of visual finding.

At least some of the systems, methods, apparatus, and/or code instructions described herein address the technical problem of automatically identifying visual findings in anatomical images. Automatic detection of visual findings in anatomical images is a challenging technical problem due to several reasons, for example, the large number of possible visual findings that may be found in anatomical images, the large number of possible combinations of visual findings that may be found in anatomical images, lack of visual clarity in identifying certain visual findings (even amongst human interpreters). For example, as described herein with reference to one implementation, any combination of 40 possible visual findings may be identified by the trained classifier. Is it noted that some combination of visual findings appear together in certain medical conditions, for example, cardiomegaly, hilar prominence, and pulmonary edema, which may be found together in the setting of congestive heart failure.

At least some of the systems, methods, apparatus, and/or code instructions described herein improve the technical field of automated analysis of anatomical images to identify visual findings. One exemplary improvement is based on the use of existing radiology reports associated with existing anatomical images (e.g., stored in PACS servers and/or EMR servers), as described herein, which allows to create very large training datasets using existing data, without requiring manual labeling of the anatomical images. As described herein, the labels are automatically generated based on the pre-created text based radiology reports associated with the anatomical images. The ability to use very large datasets improves the accuracy of the trained classifier(s). Another exemplary improvement is based on the use of two or more anatomical images captured of the patient at different orientation angles. The processing of the two or more images by the classifier increased the accuracy of classification, since for example, certain visual findings are better detected at a certain orientation and/or certain visual findings are better detected when both (or more) images are analyzed.

In another example, improvement is obtained based on the use of existing radiological reports created by radiologists interpreting the anatomical images. The use of existing radiological reports may present a technical challenge, since such reports were created for clinical purposes, to provide an interpretation to the physician that ordered the study, rather than providing a structured label for training a classifier. Use of such reports presents a technical challenge, for example, since radiologists may omit mention of normal structures in favor of brevity, thereby implying a negative label. This bias extends to many studies in which even mildly abnormal or senescent changes are omitted. For example, the same CXR may produce a single-line report of "No acute disease" by one radiologist and descriptions of cardiomegaly, and degenerative changes by another radiologist. In fact, other methods do not rely on the radiology report to create tags, but rather use a well structured labeling system in which anatomical images are annotated independently of the radiology report to create training datasets for training classifiers. Methods that do rely on the radiology report use a well defined indexing method (e.g., MeSH, as described herein in detail), while in contrast the systems, methods, apparatus, and/or code instructions described herein generate the set of positive labels based on the actual text of the reports. Moreover, the omission bias in which radiologists omit mentioning normal findings, slightly abnormal findings, findings irrelevant to the clinical indication for ordering the x-ray, abnormal findings for the general population but are commonly found in the patient's demographic group (e.g., degenerative changes commonly found in the elderly population), and/or fail to mention abnormalities observed in previous x-rays that are substantially unchanged, may introduce noise into the labeling process, particularly for findings which are not deemed critical, even in the more conservative fully-covered training set (the fully-covered training set is described in more detail below). As discussed herein, in particular in the Examples section, inventors discovered that such statistical noise that is introduced by using the radiology reports is no larger than the noise added by training a radiologist to do the tagging (i.e. "manual tagging"). Therefore, the classifier trained by using existing radiology reports for automatic generation of labels for anatomical images to create a large training dataset for training the classifier as described herein, is statistically unaffected by the introduced noise in comparison to manually tagging each anatomical image.

The manual interpretation of anatomical images performed by radiologists is a challenging task, due to the large number of possible findings that may be found. For example, the chest x-ray (CXR) is a very commonly performed radiological examination for screening and diagnosis of many cardiac and pulmonary diseases, with over 150 million obtained annually in the United States alone. CXRs are a cornerstone of acute triage as well as longitudinal surveillance Each CXR is interpreted not only for the clinical indication for which it was ordered, but to detect other abnormalities, which leads to a large number of possible findings. Human radiologists may easily miss some findings. Despite the ubiquity of the exam and its apparent technical simplicity, the chest xray is widely regarded among radiologists as among the most difficult to master, for example, as described with reference to Robinson, P. J., Wilson, D., Coral, A., Murphy, A., Verow, P.: *Variation between experienced observers in the interpretation of accident and emergency radiographs. The British journal of radiology* 72(856) (April 1999) 323-30. Moreover, there is an immense world-wide shortage of physicians capable of providing rapid and accurate interpretation of radiological studies. Due to a shortage in supply of radiologists, radiographic technicians are increasingly called upon to provide preliminary interpretations, particularly in Europe and Africa. In the US, non-radiology physicians often provide preliminary or definitive readings of CXRs, decreasing the waiting interval at the nontrivial expense of diagnostic accuracy. Even among expert radiologists, clinically substantial errors are made in 3-6% of studies, for example, as described with reference to Robinson, P. J., Wilson, D., Coral, A., Murphy, A., Verow, P.: *Variation between experienced observers in the interpretation of accident and emergency radiographs. The British journal of radiology* 72(856) (April 1999) 323-30, and Brady, A., Laoide, R., McCarthy, P., McDermott, R.: *Discrepancy and error in radiology: concepts, causes and consequences. The Ulster medical journal* 81(1) (January 2012) 3-9, with minor errors seen in 30%, for example, as described with reference to Bruno, M. A., Walker, E. A., Abujudeh, H. H.: *Understanding and Confronting Our Mistakes: The Epidemiology of Error in Radiology and Strategies for Error Reduction. RadioGraphics* 35(6) (October 2015) 1668-1676. Accurate diagnosis of some entities is particularly challenging, for example, early lung cancer is missed in 19-54% of cases, with similar sensitivity figures described for pneumothorax and rib fracture detection. The likelihood for major diagnostic errors is directly correlated with both shift length and volume of examinations being read, for example, as described with reference to Hanna, T. N., Lamoureux, C., Krupinski, E. A., Weber, S., Johnson, J. O.: *Effect of Shift, Schedule, and Volume on Interpretive Accuracy: A Retrospective Analysis of 2.9 Million Radiologic Examinations. Radiology* (November 2017) 170555, a reminder that diagnostic accuracy varies substantially even at different times of the day for a given radiologist.

At least some of the systems, methods, apparatus, and/or code instructions described herein improve the performance of a computing device that executes code instructions that implement the classifier for automatically detecting visual finding(s) in two or more anatomical images. The improvement in performance may be based on an increase in accuracy of detecting the visual findings, and/or ability to detect any combination of one or more visual findings for a set of possible visual findings, using existing computing resources (e.g., processor(s), and/or data storage). For example, the trained classifier may detect visual findings with increased sensitivity in comparison to other automated methods and/or in comparison to human ability. In another example, the improvement in performance of the computing device's ability to accurately detect visual findings depicted in the anatomical images is based on training the classifier according to the visual findings rather than, for example, training the classifier for detection of clinical interpretation and/or diagnosis. For example, training the classifier for detection of pneumonia, which is a hard-to agree upon (i.e., subjective) clinical finding, while consolidation is a more objective visual finding, which may be indicative of pneumonia. The classifier provides the user with identified visual findings, which are more objective findings, in comparison to clinical interpretation and/or diagnosis which tend to be more subjective.

At least some of the systems, methods, apparatus, and/or code instructions described herein improve an underling technical process within the technical field of medical image processing, in particular, within the field of automatic analysis of two dimensional anatomical images to identify one or more visual findings.

At least some of the systems, methods, apparatus, and/or code instructions described herein provide a unique, particular, and advanced technique of training a statistical classifier to identify visual finding(s) and applying the trained statistical classifier to identify the visual finding(s). In some implementations the unique, particular, and advanced technique is based on a mapping of individual sentences of text based radiology reports associated with the medical images to create labels indicative of visual findings in the anatomical images. In some implementations the unique, particular, and advanced technique is based on training and/or analysis of two or more anatomical images of the patient, where each anatomical image depicts a certain unique orientation of the patient and/or examined body part.

At least some of the systems, methods, apparatus, and/or code instructions described herein provide technical solutions to technical problems that are not solved by other systems and/or methods, and/or provide an improvement to the technology of automated anatomical image analysis in comparison to other systems and/or methods.

For example, Shin, H. C., Roberts, K., Lu, L., Demner-Fushman, D., Yao, J., Summers, R. M.: *Learning to read chest x-rays: Recurrent neural cascade model for automated image annotation.* In: *Computer Vision and Pattern Recognition (CVPR)* (June 2016), appears to relate to extracting labels from the 3,955 CXR reports in the OpenI dataset, using the MeSH system, for example, as described with reference to Demner-Fushman, D., Shooshan, S. E., Rodriguez, L., Antani, S., Thoma, G. R.: *Annotation of Chest Radiology Reports for Indexing and Retrieval.* (2015) 99-111. In contrast, at least some of the systems, methods, apparatus, and/or code instructions described herein create a labeling system that is based on the actual sentences of the reports, rather than using pre-existing categories and/or tags such as MeSH.

The ChestX-ray14 dataset described with reference to Wang, X., Peng, Y, Lu, L., Z.L.o.C.V., 2017, u.: *Chestx-ray8: Hospital-scale chest x-ray database and benchmarks on weakly-supervised classification and localization of common thorax diseases.* Openaccess(dot)thecvf(dot)com, contains 112 k PA images loosely labeled using a combination of NLP and hand-crafted rules. Wang et al., only relates to one particular type of anatomical image, in comparison to the systems, methods, apparatus, and/or code instructions described herein that processes two or more anatomical images at different orientations of the patient.

Rajpurkar, P., Irvin, J., Zhu, K., Yang, B., Mehta, H., Duan, T., Ding, D., Bagul, A., Langlotz, C., Shpanskaya, K., Lungren, M. P., Ng, A. Y.: CheXNet: *Radiologist-Level Pneumonia Detection on Chest X-Rays with Deep Learning.* (November 2017) relate to a team of four radiologists reported a high degree of disagreement with the provided ChestX-ray14 labels in general, although they demonstrate the ability to achieve expert-level prediction for the presence of pneumonia after training upon a DenseNet121 CNN. In contrast, at least some of the systems, methods, apparatus, and/or code instructions described herein obtain high agreement levels with human radiologists, and/or have the ability to accurately detect multiple different visual findings.

Utilizing several public datasets with image labels and reports provided, Jing, B., Xie, P., Xing, E.: *On the Automatic Generation of Medical Imaging Reports.* (November 2017) appears to relate to building a system that generates a natural appearing radiology report using a hierarchical RNN. The high-level RNN generates sentence embeddings that seed low-level RNNs that produce the words of each sentence. As part of report generation, tags representing the clinical finding present in the image were produced. However, the model trained using these tags and the text of the reports did not predict the tags better than the model that was trained just using the tags. The ultimate accuracy of the system however remains poorly defined due to lack of clinical radiologic validation. In contrast, at least some of the systems, methods, apparatus, and/or code instructions described herein create a labeling system that is based on the actual sentences of the reports, rather than using pre-existing categories and/or pre-defined tags.

Accordingly, the systems, methods, apparatus, and/or code instructions described herein are inextricably tied to computer technology and/or physical components (e.g., anatomical imaging machine, processor(s), storage device(s)) to overcome an actual technical problem arising in processing and/or analysis of anatomical images.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 2:
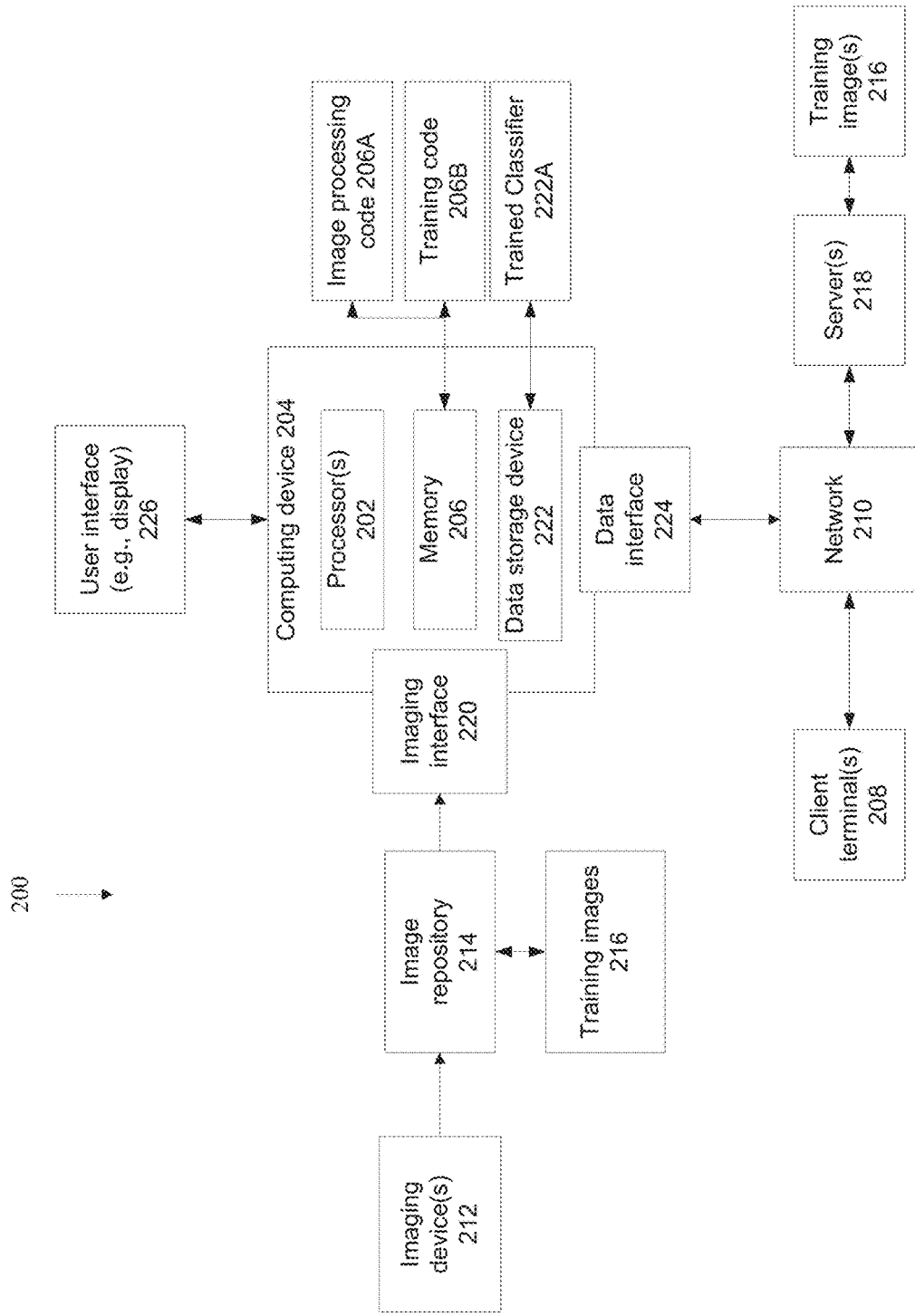
FIG. 2 is a block diagram of components of a system for identification of one or more visual findings of multiple possible visual findings in at least one of two anatomical images of a target individual and/or training a classifier for identification of one or more visual findings of multiple possible visual findings in at least one of two anatomical images of the target individual, in accordance with some embodiments of the present invention.
Figure 3:
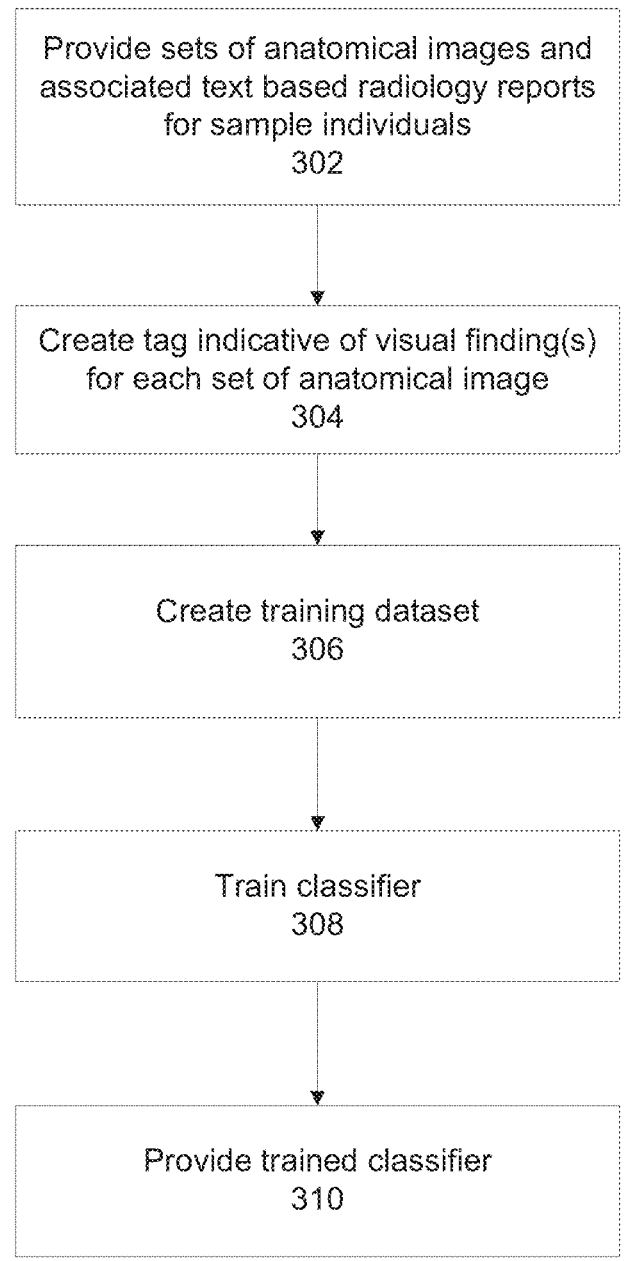
FIG. 3 is a flowchart of a method training a classifier for identification of one or more visual findings of multiple possible visual findings in at least one of two anatomical images of the target individual, in accordance with some embodiments of the present invention.

Reference is now made to FIG. 1, which is a flowchart of a method for identification of one or more visual findings of multiple possible visual findings in at least one of two anatomical images of a target individual, in accordance with some embodiments of the present invention. Reference is also made to FIG. 2, which is a block diagram of components of a system 200 for identification of one or more visual findings of multiple possible visual findings in at least one of two anatomical images of a target individual and/or training a classifier for identification of one or more visual findings of multiple possible visual findings in at least one of two anatomical images of the target individual, in accordance with some embodiments of the present invention. Reference is also made to FIG. 3, which is a flowchart of a method training a classifier for identification of one or more visual findings of multiple possible visual findings in at least one of two anatomical images of the target individual, in accordance with some embodiments of the present invention. System 200 may implement the acts of the method described with reference to FIG. 1 and/or FIG. 3, optionally by a hardware processor(s) 202 of a computing device 204 executing code instructions stored in a memory 206.

Computing device 204 may be implemented as, for example, a client terminal, a server, a virtual server, a radiology workstation, a virtual machine, a computing cloud, a mobile device, a desktop computer, a thin client, a Smartphone, a Tablet computer, a laptop computer, a wearable computer, glasses computer, and a watch computer. Computing 204 may include an advanced visualization workstation that sometimes is add-on to a radiology workstation and/or other devices for presenting indications of the identified visual findings and/or other computer added detections to the radiologist.

Computing device 204 may include locally stored software that performs one or more of the acts described with reference to FIG. 1 and/or FIG. 3, and/or may act as one or more servers (e.g., network server, web server, a computing cloud, virtual server) that provides services (e.g., one or more of the acts described with reference to FIG. 1 and/or FIG. 3) to one or more client terminals 208 (e.g., remotely located radiology workstations, remote picture archiving and communication system (PACS) server, remote electronic medical record (EMR) server) over a network 210, for example, providing software as a service (SaaS) to the client terminal(s) 208, providing an application for local download to the client terminal(s) 208, as an add-on to a web browser and/or a medical imaging viewer application, and/or providing functions using a remote access session to the client terminals 208, such as through a web browser.

Is it noted that the training of the classifier, and the application of the trained classifier to anatomical images to identify visual findings, may be implemented by the same computing device 204, and/or by different computing devices 204, for example, one computing device 204 trains the classifier, and transmit the trained classifier to a server device 204.

As used herein, the terms anatomical imaging device and anatomical imaging sensor may sometimes be interchanged.

Computing device 204 receives 2D images, and/or a set of Mammographic 2D images (two or more views per breast) and/or 2D slices (optionally extracted from 3D imaging data at different slicing planes that are non-parallel to one another, for example extracted from a 3D mammographic scan) captured by an anatomical imaging device(s) 212, for example, an x-ray machine, a magnetic resonance imaging (MRI) device, a computer tomography (CT) machine, and/or an ultrasound machine. Anatomical images captured by imaging machine 212 may be stored in an image repository 214, for example, a storage server, a computing cloud, virtual memory, and a hard disk. The anatomical images stored by image repository 214 may include images of patients optionally associated with text based radiology reports. Training images 216 are created based on the captured anatomical images and text based radiology reports, as described herein.

Training images 216 are used to train the classifier, as described herein. It is noted that training images 216 may be stored by a server 218, accessibly by computing device 204 over network 210, for example, a publicly available training dataset, and/or a customized training dataset created for training the classifier, as described herein.

Anatomical images captured by imaging machine(s) 212 depict anatomical features and/or anatomical structures within the body of the target patient.

Computing device 204 may receive the training images 216 from imaging device 212 and/or image repository 214 using one or more imaging interfaces 220, for example, a wire connection (e.g., physical port), a wireless connection (e.g., antenna), a local bus, a port for connection of a data storage device, a network interface card, other physical interface implementations, and/or virtual interfaces (e.g., software interface, virtual private network (VPN) connection, application programming interface (API), software development kit (SDK)).

Hardware processor(s) 202 may be implemented, for example, as a central processing unit(s) (CPU), a graphics processing unit(s) (GPU), field programmable gate array(s) (FPGA), digital signal processor(s) (DSP), and application specific integrated circuit(s) (ASIC). Processor(s) 202 may include one or more processors (homogenous or heterogeneous), which may be arranged for parallel processing, as clusters and/or as one or more multi core processing units.

Memory 206 (also referred to herein as a program store, and/or data storage device) stores code instruction for execution by hardware processor(s) 202, for example, a random access memory (RAM), read-only memory (ROM), and/or a storage device, for example, non-volatile memory, magnetic media, semiconductor memory devices, hard drive, removable storage, and optical media (e.g., DVD, CD-ROM). For example, memory 206 may store image processing code 206A that implement one or more acts and/or features of the method described with reference to FIG. 1, and/or training code 206B that execute one or more acts of the method described with reference to FIG. 3, and/or code instructions of trained classifier 222A.

Computing device 204 may include a data storage device 222 for storing data, for example, a trained classifier 222A (as described herein), training images 216, and/or text based radiology reports. Data storage device 222 may be implemented as, for example, a memory, a local hard-drive, a removable storage device, an optical disk, a storage device, and/or as a remote server and/or computing cloud (e.g., accessed over network 210). It is noted that trained classifier 222A, training images 216, and/or text based radiology reports may be stored in data storage device 222, with executing portions loaded into memory 206 for execution by processor(s) 202.

Computing device 204 may include data interface 224, optionally a network interface, for connecting to network 210, for example, one or more of, a network interface card, a wireless interface to connect to a wireless network, a physical interface for connecting to a cable for network connectivity, a virtual interface implemented in software, network communication software providing higher layers of network connectivity, and/or other implementations. Computing device 204 may access one or more remote servers 218 using network 210, for example, to download updated training images 216 and/or to download an updated version of image processing code, training code, and/or the trained classifier.

Computing device 204 may communicate using network 210 (or another communication channel, such as through a direct link (e.g., cable, wireless) and/or indirect link (e.g., via an intermediary computing device such as a server, and/or via a storage device) with one or more of:

Client terminal(s) 208, for example, when computing device 204 acts as a server providing image analysis services (e.g., SaaS) to remote radiology terminals, for analyzing remotely obtained anatomical images.

Server 218, for example, implemented in association with a PACS, which may storage large numbers of anatomical images and/or radiology reports for analysis, for example, captured by an imaging machine of a radiology clinic.

Anatomical image repository 214 that stores anatomical images and/or imaging device 212 that outputs the anatomical images.

It is noted that imaging interface 220 and data interface 224 may exist as two independent interfaces (e.g., two network ports), as two virtual interfaces on a common physical interface (e.g., virtual networks on a common network port), and/or integrated into a single interface (e.g., network interface).

Computing device 204 includes or is in communication with a user interface 226 that includes a mechanism designed for a user to enter data (e.g., patient data) and/or view the indications of identified visual findings. Exemplary user interfaces 226 include, for example, one or more of, a touchscreen, a display, a keyboard, a mouse, and voice activated software using speakers and microphone.

Referring now back to FIG. 1, at 102, the statistical classifier is provided and/or trained.

Multiple classifiers may be trained. Each classifier may be trained to process a certain set of anatomical images outputted by a certain anatomical imaging device. For example, a certain classifier is trained to analyze chest x-rays in which one anatomical image depicts the patient in an AP orientation, and another image depicts the patient in a lateral orientation. In another example, another classifier is trained to analyze abdominal x-rays in which one anatomical image depicts the patient lying down, and another image depicts the patient upright (e.g., sitting, standing). In another example, another classifier is trained to analyze x-rays of the shoulder at three more or more distinct orientations. In another example, another classifier is trained to analyze mammography images of the breast in which one anatomical image depicts the MLO view of the breast, and another image depicts the CC view of the same breast. It is noted that other views of the breast may be implemented.

The classifier may be selected from multiple available classifiers. The selection may be performed manually by the user (e.g., via a user interface, for example, displaying a menu and/or icons of available classifiers). The selection may be performed automatically by code that determines the orientation of the patient in the image and/or the imaging modality, for example, by an analysis of metadata associated with each image and/or code that analyzes the images themselves.

An exemplary method of training the one or more classifiers is described with reference to FIG. 3.

At 104, two (or more) anatomical images depicting a body portion of a target individual are provided.

Each of the two (or more) anatomical images is depicts a unique orientation of at least the body portion of the target individual, for example, whole body orientation (e.g., AP, PA, lateral) and/or limb orientation (adduction, abduction, internal rotation, external rotation) and/or body position (e.g., sitting down, standing up).

For example, a first anatomical image is captured when the target individual is oriented laterally relative to an anatomical imaging device, and a second anatomical image is captured when the target individual is oriented anterior-posterior (AP) or posterior-anterior (PA) relative to the anatomical imaging device, for example, in the case of a chest x-ray. In another example, a first anatomical image is captured when the target individual is oriented supine relative to an anatomical imaging device, and a second anatomical image is captured when the target individual is oriented upright relative to the anatomical imaging device, for example, in the case of abdominal x-ray.

The images may be obtained, for example, from a PACS server, an EMR server, from the anatomical imaging device, and/or from a storage device (e.g., portable storage medium, storage server). For example, anatomical images are automatically sent to analysis after capture by the imaging modality and/or once the images are stored.

Exemplary body portions include: a chest, an abdomen, breast, and a limb (e.g., joint, and/or portion of a limb, such as shoulder, hip, wrist, and elbow).

Exemplary anatomical imaging device includes an x-ray machine that captures a two dimensional anatomical image.

At 106, a certain anatomical image (of the two anatomical images) is fed into a certain convolutional neural network (CNN) of a statistical classifier. The certain CNN outputs a respective feature vector.

The certain CNN is designed to process anatomical images depicting a defined orientation of the target individual. For example, only chest x-rays in which the target individual is laterally oriented.

At 108, the other anatomical image of the two anatomical images is fed into the other CNN of the statistical classifier. The other CNN outputs a respective feature vector.

The other CNN is designed to process anatomical images depicting another defined orientation of the target individual. For example, only chest x-rays in which the target individual is AP oriented.

Is it noted that the case of two CNNs is exemplary and not necessarily limiting. The statistical classifier may be designed to include three or more CNNs when three or more anatomical images each depicting a unique orientation of the target patient are available, for example, in the case of should x-rays.

Each CNN may be implemented, for example, based on DenseNet 121 described with reference to Huang, G., Liu, Z., van der Maaten, L., Weinberger, K. Q.: *Densely connected convolutional networks. In: Proceedings of the IEEE Conference on Computer Vision and Pattern Recognition.* (2017), which is trained separately according to each type of corresponding anatomical image (i.e., different patient orientations, for example, for chest x-ray PA view and for lateral view).

At 110, the feature vectors outputted by respective CNNs are combined, optionally concatenated, and fed into a fully connected layer of the statistical classifier. The feature vectors may be extracted just after the average pooling layer. The fully connected layer is customized.

At 112, the fully connected layer computed an indication of one or more distinct visual findings (from a set of possible visual findings that may be detected by the trained classifier) present in one or both of the two anatomical images. The fully connected layer may output a finding for each possible visual finding indicating whether the respective visual finding is identified within one or both images or not. Alternatively, only the visual findings identified within one or both images are outputted. Alternatively, a probability score is outputted for each respective visual finding indicative of the probability of each respective visual findings being depicted within one or both images.

The output of the fully connected layer may be followed by a sigmoid activation function to output probabilities of the respective visual findings being present in one or more of the images.

The set of possible visual findings may be determined according to an analysis of sentences of radiologist reports associated with anatomical images of the sample individuals of the training dataset, as described herein.

Exemplary visual findings for chest x-rays include: abnormal aorta, aortic calcification, artificial valve, atelectasis, bronchial wall thickening, cardiac pacer, cardiomegaly, central line, consolidation, costrophrenic angle blunting, degenerative changes, elevated diaphragm, fracture, granuloma, hernia diaphragm, hilar prominence, hyperinflation, interstitial markings, kyphosis, mass, mediastinal widening, much bowel gas, nodule, orthopedic surgery, osteopenia, pleural effusion, pleural thickening, pneumothorax, pulmonary edema, rib fracture, scoliosis, soft tissue calcification, sternotomy wires, surgical clip noted, thickening of fissure, trachea deviation, transplant, tube, and vertebral height loss. Exemplary visual findings for mammography include: masses, calcifications, calcified masses, calcification clusters, distortions, asymmetries, densities and scars.

Optionally, the statistical classifier computes a confidence score indicative of a probability of the presence of each respective visual finding in at least one of the two (or more) anatomical images. Alternatively, the classifier outputs an absolute value indicative of the presence of the visual finding(s), and optional the absence of other visual finding(s).

The output of the fully connected layer may be an array and/or vector, where each element of the array corresponds to one of the possible visual findings that may be identified by the trained classifier. For example, the first element corresponds to abnormal aorta, the second element corresponds to aortic calcification, and so on. The value within each element may be a binary value (e.g., 0 or 1, TRUE or FALSE) indicating the presence or absence of the respective visual finding. The value within each element may be the confidence score indicative of the probability of the presence of the respective visual finding.

Optionally, a heat map is computed according to the confidence score for each of the visual findings. The heat map may be computed per image. The heat map may be computed according to the vectors outputted by each of the CNN, for example, the heat map is generated as a linear combination over the feature maps calculated for each anatomical image. The feature maps may be obtained from the output of the network's third-to-last layer (i.e., in the second-to-last layer each "feature map" may be reduced to a single number in the resulting feature vector, and the last layer is the fully-connected layer which generates the output probability of each finding). The weight assigned to feature map i when generating a heat map for visual finding j may be denoted $W_{ij}$, where W denote the matrix of weights of the last fully connected layer of the network. The heat map may be presented as an overlay of one or both of the images. For example, colors and/or intensity levels may be computed for pixels of the images according to the probability of a visual finding at the corresponding pixels.

Optionally, the classifier outputs a single indication for multiple visual findings of the same type, for example, when two more rib fractures are depicted in the anatomical images, the classifier outputs the indication "rib facture". The multiple visual findings of the same type may be located at different locations within the anatomical images, for example, on the left side of the patient, on the right side of the patient, towards the head, and/or towards the feet.

Referring now back to FIG. 1, at 114, the computed indication of distinct visual findings are provided.

Optionally, the indications visual findings are stored in a data stored device (e.g., in association with the medical images such as a metadata tag, and/or stored in the EMR of the patient, and/or in the PACS server).

Alternatively or additionally, the indications visual findings are forwarded, for example, over a network to a remote server and/or client terminal and/or mobile device.

Alternatively or additionally, the indications visual findings are presented on a display, for example, a list of the indication of visual findings is presented as a pop-up window on the screen, optionally while the images are presented.

Referring now back to FIG. 3, at 302, sets of anatomical images are provided for each of multiple sample individuals. Each set of anatomical images includes two or more images of a body portion of the respective sample individual depicting a respective unique orientation of at least the body portion of the respective sample individual. A text based radiology report, which includes one or more sentences is associated with the anatomical images. The text based radiology report includes a description of the radiological reading of the images, for example, typed by radiologist, or transcribed from a verbal dictation provided by the radiologist.

The sets of anatomical images and associated radiology report may be obtained, for example, from a PACS server, and/or EMR records of the sample individuals.

At 304, a respective tag is created for each set of anatomical images of each sample individuals. Each tag includes one or more visual findings depicted in one or both of the images. The tags may be implemented as, for example, a metadata tags, electronic labels, and/or pointers to entries in a dataset (e.g., an array where each element denotes a distinct visual findings).

The tags are created according to an analysis that maps individual sentences of each respective radiology report to corresponding indications of distinct visual findings depicted in the anatomical images associated with the respective radiology report. An individual sentence is mapped to one of the distinct visual findings.

A set of distinct visual findings is created according to an analysis of the sentences (optionally all sentences) of the radiology reports of the images. The indications of distinct visual findings are based on visual findings that are identified by radiologists. However, since different radiologists may use different sentences and/or different terms to refer to the same visual finding, multiple different sentences may map to the same distinct visual finding.

Optionally, the individual sentences from the radiology reports of the sample individuals are clustered into a relatively small number of distinct visual findings, for example, about 10 visual findings, or about 20, or about 25, or about 30, or about 40, or about 50, or about 100. The number of radiology reports is small in comparison to the number of distinct sentences, for example, about 500,000, or about 1 million sentences. Each cluster denotes one of the distinct visual finding. All sentences within the respective cluster are indicative of same respective distinct visual finding. The clustering may be performed, for example, manually by users, and/or based on supervised and/or unsupervised machine learning methods that are designed to create clusters.

Clustering may be performed according to one or more of the following: clustering could have many options:

1. Manually going over some of the more-frequent sentences and tagging them (e.g., as described in the experiment in the Examples section).

2. Using algorithm(s) to automatically parse sentences in the reports and associate them to positive findings (or negative).

3. The algorithm(s) in (2) may be rule-based (e.g., for each finding, a human writes a formula, and if the sentence satisfies this formula, the sentence is mapped to a positive indication of the finding).

4. The algorithm(s) in (2) may learn the formula automatically (i.e. ML algorithm) given a sample of manually annotated sentences (such as the ones in (1)).

At 306, one or more training datasets are created for training one or more classifiers. Each training dataset includes sets of anatomical images and associated tags.

The training datasets may be sorted according to the target classifier being trained, for example, according to body portion being imaged, according to image modality, and/or according to orientation of the body portion of the patient appearing in the images.

Optionally, the training dataset is created by mapping a sub-set of sentences of the text based radiology reports (optionally one or more sentences from each report) of the sample individuals that are indicative of positive findings (i.e., a visual finding which may be abnormal) to one of the indications of visual findings. The negative sentences are either ignored (as described in the experiment in the Example section), or mapped to negative labels for the mentioned visual findings in the sentence. The neutral sentences are just ignored, as they convey no indicative information. The ambiguous sentences may lead to the removal of the associated set of images from the training set.

In another example, another sub-set of sentences denoting negative findings (e.g., normal findings, or lack or abnormal finding), and/or neutral data (i.e., does not indicate a positive or negative finding), and/or ambiguous data (e.g., unclear whether the data indicates a positive or negative finding) is mapped to another tag indicative of no visual findings. The other sub-set of sentences are not mapped to any one of the indications of visual findings. The classifier may be trained on both sub-sets of sentences and associated anatomical images, where one sub-set trains the classifier to identify the visual findings, and the other sub-set trains the classifier to avoid false positives by incorrectly designating negative finding as visual findings.

Sentences denoting neutral findings may be ignored.

Optionally, a fully covered training dataset is created according to a sub-set of the text based radiology reports of the sample individuals (i.e., some reports are excluded from the training dataset). For each respective textbased radiology report included in the sub-set, each one of the sentences of the respective text based radiology report is mapped to one of: one of the indications of visual findings (i.e., denoting a positive finding from the findings supported by the model), a negative finding, and neutral data. The classifier may be trained according to the fully covered training dataset and associated anatomical images.

Alternatively, an any hit training dataset is created according to a sub-set of the text based radiology reports of the sample individuals (i.e., some reports are excluded from the training dataset). For each respective text based radiology report included in the sub-set, at least one of the sentences of the respective text based radiology report is mapped to one of the indications of visual findings. Sentences mapping to negative findings and/or neural data are ignored. The classifier may be trained according to the any hit training dataset and associated anatomical images.

At 308, one or more statistical classifiers are trained according to the created training dataset(s).

The classifier is trained for identification of one or more visual findings from the possible visual findings in one or both anatomical images of the body portion of the target individual.

Optionally, the classifier includes a first CNN that computes a first feature vector according to an inputted first anatomical image, a second CNN designed to output a second feature vector according to an inputted second anatomical image of the two anatomical images, and a fully connected layer that outputs an indication of one or more visual findings according to a concatenation of the first feature vector and the second feature vector.

Optionally, the statistical classifier is trained according to a main loss function based on a mean of binary cross-entropy losses, for example:

$$loss = \frac{1}{K}\sum_{k=1}^{K} y_k \log(p_k) + (1 - y_k)\log(1 - p_k)$$

Where:

$p_k$ denotes the value of the k-th output unit, and $y_k$ denotes the binary label for the k-th finding.

At 310, the trained statistical classifier is provided. The trained statistical classifier may be locally stored by the computing device, and/or forwarded to the computing device when the training is performed by another device.

Figure 4:
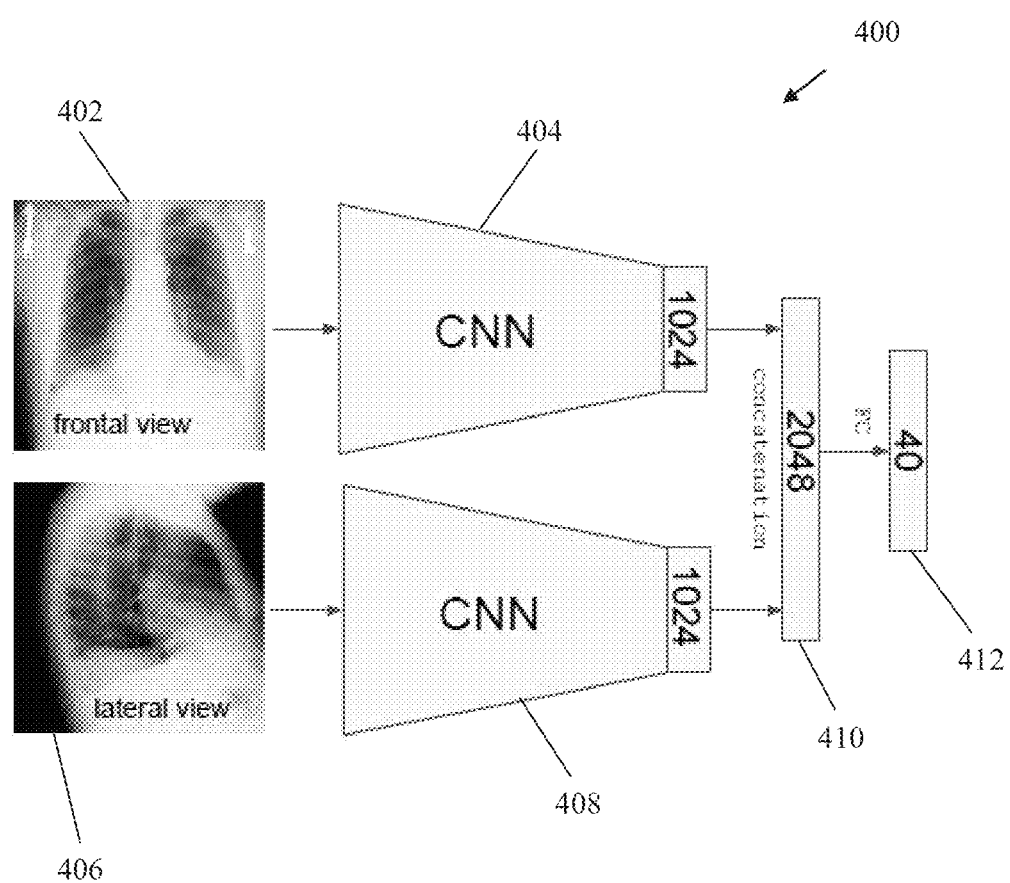
FIG. 4 is a schematic of an architecture of a classifier for computing indication(s) of visual findings in anatomical images, in accordance, with some embodiments of the present invention.

Reference is now made to FIG. 4, which is a schematic of an architecture of a classifier 400 for computing indication(s) of visual findings in anatomical images, in accordance, with some embodiments of the present invention. A frontal view chest x-ray 402 is inputted into a CNN 404 that outputs a respective feature vector, optionally including 1024 features and/or of size 1024 (e.g., as described with reference to act 106 of FIG. 1). A lateral view chest x-ray 406 is inputted into another CNN 408 that outputs a respective feature vector, optionally including 1024 features and/or of size 1024 (e.g., as described with reference to act 108 of FIG. 1). The feature vectors outputted by CNN 404 and CNN 408 are concatenated into a concatenation data structure 410 (e.g., as described with reference to act 110 of FIG. 1). Concatenation data structure 410 is inputted into a fully connected layer 412, which computes one or more indications of visually distinct findings depicted in one or both images 402 and 406 (e.g., as described with reference to act 112 of FIG. 1). For example, one or more of 40 possible visual findings. Alternatively or additionally, fully connected layer 412 computes a probability score for each of the 40 possible visual findings indicative of likelihood of the respective visual finding being depicted in one or both of images 402 and 406.

Figure 5:
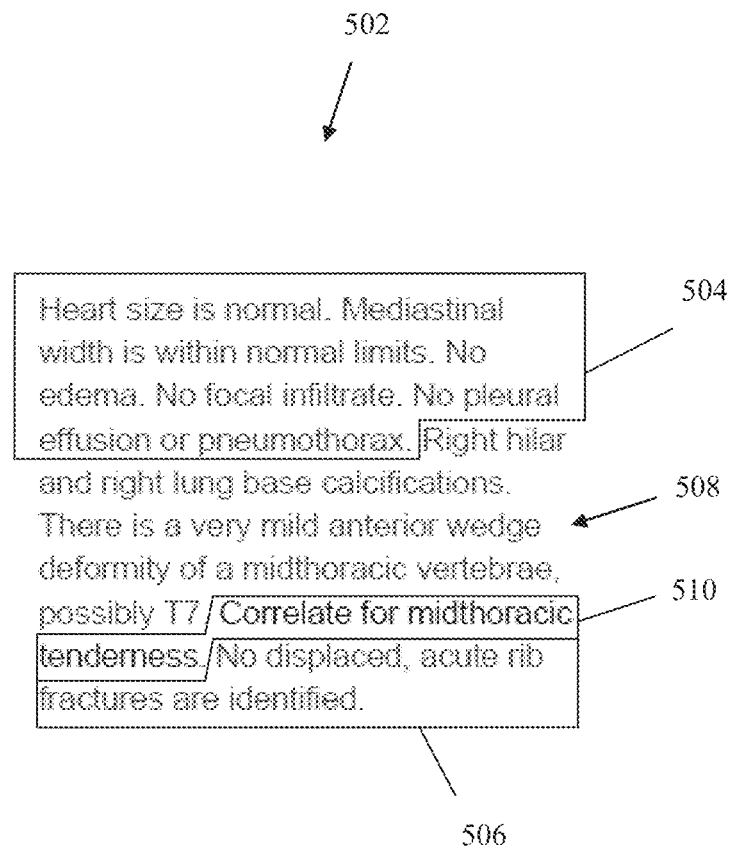
FIG. 5 is a schematic depicting an example of an analysis of sentences of a text based radiology report for generation of training tags (also referred to herein as labels), in accordance with some embodiments of the present invention.

Reference is now made to FIG. 5, which is a schematic depicting an example of an analysis of sentences of a text based radiology report 502 for generation of training tags (also referred to herein as labels), in accordance with some embodiments of the present invention. Radiology report 502 includes multiple verbal sentences, based on the radiologist's personal style, which described findings in the x-ray images. Sentences 504 and 506 represent negative findings, i.e., no visual findings. The negative findings may represent normal findings. Sentences with negative findings are assigned a negative label. Sentences 508 represent visual findings in the x-ray images. Sentences representing visual findings are mapped to one of the possible visual findings. Sentence 510 represents a neural finding, which does not indicate a positive visual finding or a negative/normal visual finding. Sentences representing neutral findings may be ignored.

Figure 6:
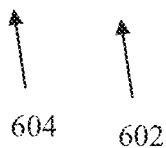
FIG. 6 is a set of possible exemplary visual findings depicted in the anatomical images, in accordance with some embodiments of the present invention.

Reference is now made to FIG. 6, which is an example of a set of possible visual findings 602 depicted in the anatomical images, in accordance with some embodiments of the present invention. The possible visual findings 602 may be identified based on a clustering of the sentences of the reports of the sample individuals, for example, as described herein. Optionally, array 604 is outputted by the classifier (i.e., by the fully connected layer), where each element including a value of 0 indicates that the corresponding visual finding (i.e., corresponding row of column 602) is not identified in the set of anatomical images. A value of 1 indicates that the corresponding visual finding (i.e., corresponding row of column 602) is identified as being depicted in the set of anatomical images. In the example shown, vertebral height loss, hilar, and granuloma are identified as visual findings for the set of anatomical images.

Various embodiments and aspects of the present invention as delineated hereinabove and as claimed in the claims section below find calculated support in the following examples.

EXAMPLES

Reference is now made to the following examples of training the statistical classifier and analysis of anatomical images by the trained statistical classifier, which together with the above descriptions illustrate some implementations of the systems, methods, apparatus, and/or code instructions described herein in a non limiting fashion.

Inventors performed a computational evaluation according to the systems and/or methods and/or apparatus and/or code instructions described herein, based on the features and/or system components discussed with reference to FIGS. 1, 2 and 3.

For creation of the training dataset, all Patient Health Information (PHI) was removed from the data prior to acquisition in compliance with HIPAA standards. A dataset of 2.1 million chest x-rays (CXRs) with their respective text based radiology diagnostic reports was used. All posteroanterior (PA) C×R images of individuals aged 18 and above were procured. Corresponding lateral views were present in 85% of the CXR examinations and were included in the training data.

A standardization process was employed whereby all CXR reports were reduced to a set of distinct canonical labels. A sentence boundary detection algorithm was applied to the 2.1M reports corresponding to the CXR, yielding a pool of 827 k unique sentences. Three expert radiologists and two medical students categorized the most occurring sentences with respect to their pertinence to C×R images. Inventors discovered that the sentences may be clustered into three categories: (1) Sentences that report the presence or absence of a finding, for example "the heart is enlarged", or "normal cardiac shadow", and therefore used for generating a label. (2) Neutral sentences, which referenced information not derived from or inherently related to the image itself, for example: "84 year old man with cough", "lung nodule follow up", or "comparison made to CT chest". (3) Sentences that may render the study unreliable for training due to ambiguity regarding the relationship of the text to the image, for example "no change in the appearance of the chest since yesterday".

After filtering out neutral and negative sentences using a few hand-crafted regular expressions, it was possible to fully cover 826 k reports using just the 20 k most prevalent positive sentences. The same expert radiologists reviewed each of these sentences and mapped them to an initial ontology of 60 findings which covered 99.99% of all positive sentence volume.

To create a final ontology for training the classifier, visual findings were selected rather than clinical interpretations or diagnoses. Some categories were merged: osteoporosis was merged into osteopenia, twisted and uncoiled aorta into abnormal aorta, and bronchial markings into interstitial markings, since it is often impossible to differentiate these findings based on the image alone. Although visually distinct, all tubes and venous lines were consolidated into two respective categories.

Reference is now made to FIG. 7, which includes a table of the top 40 visual findings identified from the radiology reports associated with the training images, in accordance with some embodiments of the present invention. It is noted that 596 k (62%) of the total 959 k studies had not reported findings.

On completion of sentence labeling, the appropriate training set was designed. It is noted that a conservative approach would only include studies whose report sentences were fully-covered (the fully-covered set is created as described herein), i.e. every potentially positive sentence in each study was manually reviewed and mapped to a finding. A more permissive any-hit approach would include any study with a recognized positive sentence in its report, ignoring other unrecognized sentences, with the risk that some of them also mention abnormalities that would be mislabeled as negatives.

The fully-covered approach yielded 596 k normal studies (i.e., no positive findings), and 230 k abnormal studies (i.e., at least one positive finding). The any-hit approach, while noisier, added 58% more abnormal studies, for a total of 363 k. The final training set included 826 k studies in the fully-covered approach, and 959 k studies in the any-hit approach.

Inventors performed computational evaluations to evaluate compare both the fully-covered and any-hit approaches. The larger any-hit training set was set as a baseline. The training set was partitioned into training, validation, and testing (80%/10%/10% respectively), based on the (anonymized) patient identity. From the 10% of studies designated as validation, a validation set of size 994 was compiled with at least 25 positives from each finding. The classifier with the lowest validation loss was selected.

The classifier designed for the experiments received 2 inputs of size 299×299. When lateral view was unavailable, the classifier was fed with random noise instead. Each X-Ray image (up to 3000×3000 pixels in raw format) was zero-mean-normalized, rescaled to a size of 330(1+a)×330 (1+b), and rotated c degrees. A random patch of 299×299 was taken as input. For training augmentation, a, b were uniformly sampled from +/−0.09 and c from +/−9, and each image was randomly flipped horizontally. For balance, the PA view was replaced with random noise in 5% of the samples. For test a=b=c=0 and central patch was used as input, without flipping.

The classifier was trained on two 1080Ti GPUs, where each CNN of the classifier was trained on a different GPU. The built-in Keras 2.1.3 implementation of DenseNet121 over Tensorow 1.4 were used. The Adam optimizer with Keras default parameters was used, and a batch size was 32. The studies were sorted in two queues, normal and abnormal. Each, batch was filled with 95% abnormal studies on average. An epoch was defined as 150 batches. The starting learning rate was 0.001, which was multiplied by 0.75 when validation loss hadn't improved for 30 epochs. The classifier was trained for 2000 epochs.

12 of the 40 visual finding categories were selected. Evaluation sets were created according to the selected 12 visual findings, using studies from the test partition. Most sets focused on a single finding except cardiomegaly, hilar prominence, and pulmonary edema, which were lumped together as these visual findings are commonly seen in the setting of congestive heart failure. In each set, the studies were derived from two pools. The first pool, termed pos-pool, included studies for which the radiology reports included a positive indicative for that respective visual finding. The studies included in the pos-pool were obtained by a manual textual search for terms indicative for each finding, independently of the sentence-tagging operation. The second pool, termed neg-pool, included randomly sampled studies, which were mostly negative for any finding.

Reference is now made to FIG. 8, which includes a table summarizing the composition of the evaluation sets, in accordance with some embodiments of the present invention. Textray denotes the trained classifier described herein. The number of studies obtained from the pos-pool (i.e., finding is positive in the radiology report) and neg-pool (i.e., random sample) are presented in the table, along with the average agreement rate (AAR) of the 3 radiologists (denoted as rads) assigned to each set versus the radiology report. The AAR between the results obtained by the classifier described herein and the rads (i.e., denoted by the column textray) is compared against the AAR between any radiologist and the other rads (denoted as avg rad). Confidence intervals are computed over the difference (denoted A).

Each set was evaluated by three expert radiologists. In each set, the radiologist reviewed the shuffled studies and indicated the presence or absence of the relevant visual finding, using a web-based software operated on a desktop. The radiologists were shown both PA and Lateral view in their original resolutions.

The radiology report was considered as a fourth expert opinion. To measure the accuracy of the label-extraction process, the report opinion was cross referenced with the training set labels. The positive labels in the training set were accurately mentioned the report; frequently, positive findings mentioned in the reports was mislabeled as negatives, as would be expected in the any-hit training set, but this was also observed to lesser degree even in the fully-covered set.

Reference is now made to FIG. 9, which is a table summarizing the percent of positive studies that included the 12 visual findings of the evaluation set, and the percent of the positive studies that had correct label assignments, in accordance with some embodiments of the present invention. The table presents an estimation of label noise in the two training described herein.

The fully-covered training set includes a study when all potentially positive sentences of the respective radiology report are parsed and mapped to respective findings. The any-hit training set includes a study when at least one sentence is parsed and mapped to a finding, even when the rest of the positive sentences were not parsed and their findings are unknown. The any-hit training set includes more positive studies for every finding (left 2 columns), but a larger portion of those positive findings is erroneously labeled as negative (right 2 columns).

A pairwise analysis of the radiologist agreement was performed following the procedure described with reference to Rajpurkar, P., Irvin, J., Zhu, K., Yang, B., Mehta, H., Duan, T., Ding, D., Bagul, A., Langlotz, C., Shpanskaya, K., Lungren, M. P., Ng, A. Y.: *CheXNet: Radiologist-Level Pneumonia Detection on Chest X-Rays with Deep Learning.* (November 2017), except that the inventors used the agreement rate between two taggers (e.g., accuracy) instead of the F1 score. This adjustment was made by the inventor because (a) the agreement rate also measures agreement on the negatives; and (b) the agreement rate is easier to interpret. The average agreement rate (AAR) for a radiologist (or a model) is the average of the agreement rates achieved against the other two (three for a model) radiologists. The average radiologist rate is the mean of the three radiologists' AARs. The bootstrap method (n=10000) was used to obtain 95% confidence intervals over the difference between the classifier described herein and the average radiologist agreement rates. As the threshold for the classifier for each finding, the one that maximized the AAR on the validation set was used.

Referring now back to FIG. 8, the table shows that the classifier described herein (termed textray) is on par with human radiologists (within the 95% CI) on 10 out of 12 findings, with the exception of rib fracture and hilar prominence. It is noted that for some findings (elevated diaphragm, abnormal aorta, and pulmonary edema), radiologists agree significantly more with the output of the classifier described herein than with each other. The table of FIG. 8 also shows the average agreement of the radiologists with the report. In this case as well, the agreement is often higher than the average agreement among the radiologists themselves. These results provide evidence that the noise added by using the reports as labels is no larger than the noise added by training a radiologist to do the tagging.

Using the text-based labels as ground-truth, the performance of the trained classifier described herein was tested over all 40 visual finding categories. To create the test set, a random sample of 5,000 studies was selected from the test partition. More studies were added from the partition until each finding had at least 100 positive cases, for a total of 7,030 studies.

Reference is now made to FIG. 10, which includes multiple ROC plots of the trained classifier for each of the 40 visual findings of chest x-ray findings described in the experiment, in accordance with some embodiments of the present invention. The title of each ROC plot indicates the number of positive in the text set of 7030 studies. The AUC and the accuracy when sensitivity=specificity is indicated on each plot. The AUCs for the 40 visual findings range between 0.7 and 1.0 (average 0.892). It is noted that at the top of the chart, artificial objects (i.e. pacers, lines, tubes, wires, and implants) are detected with AUCs approaching 1.0, much better than all diseases.

Figure 11:
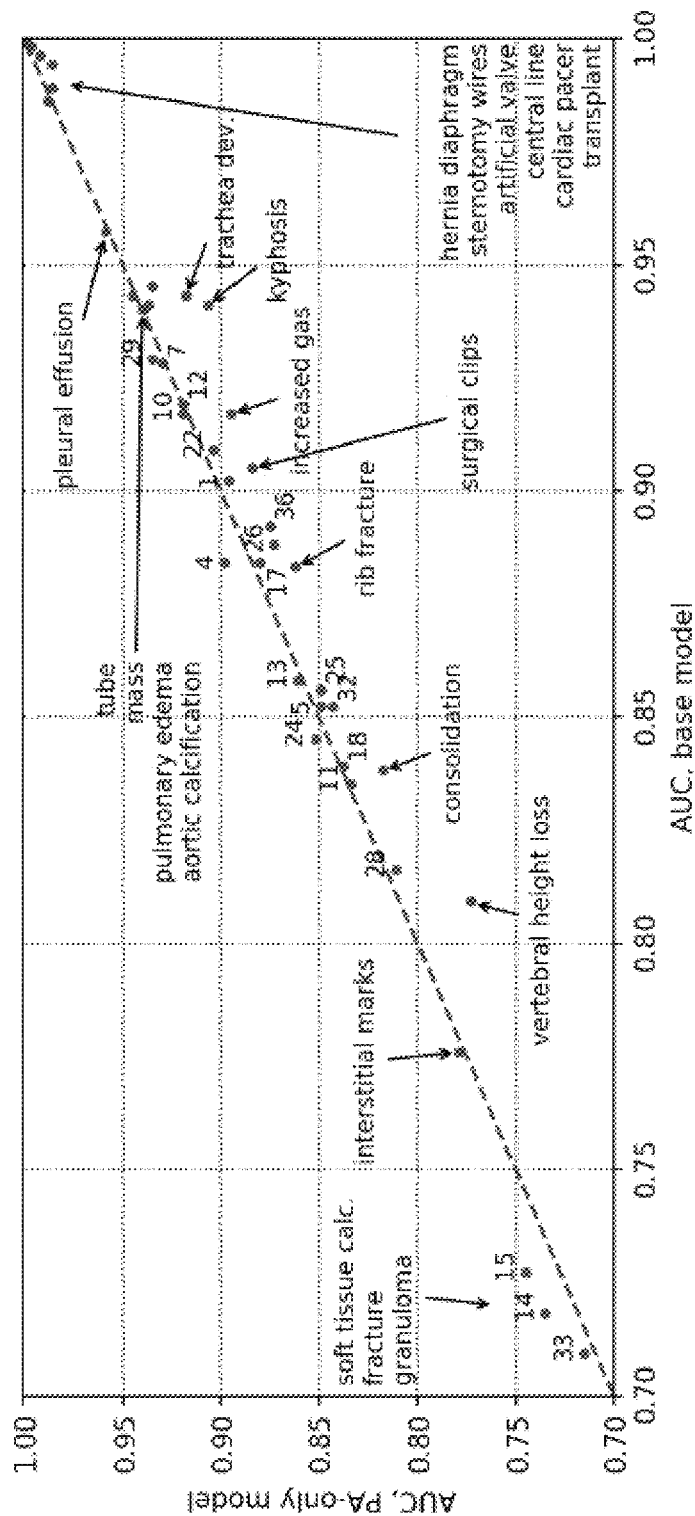
FIG. 11 a graph of the area under the ROC curve (AUC) achieved by the trained classifier compared to a variant that was trained only with the PA view of each study of the experiment, in accordance with some embodiments of the present invention.
Figure 13:
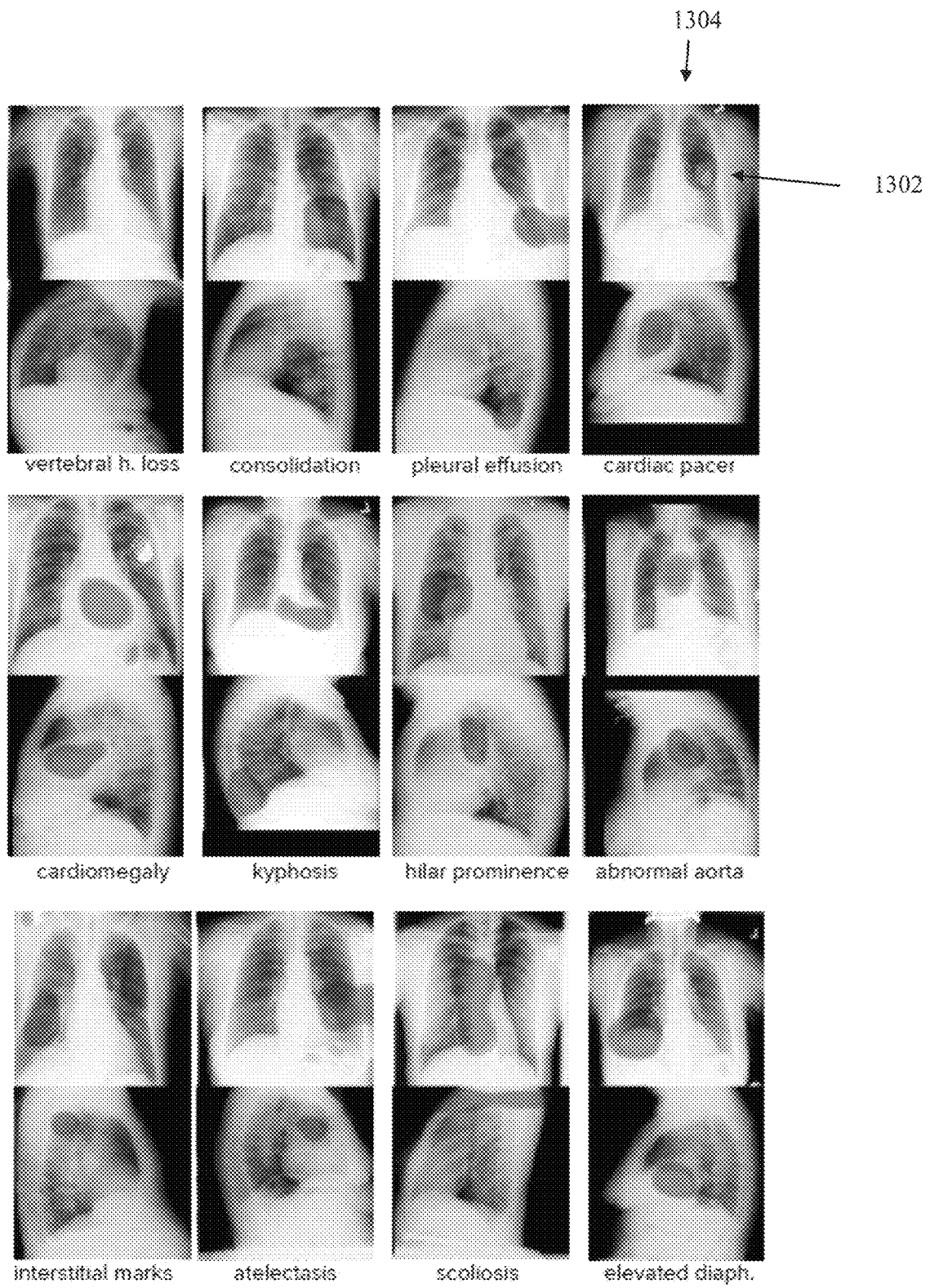

Reference is now made to FIG. 11, which is a graph of the area under the ROC curve (AUC) achieved by the trained classifier compared to a variant that was trained only with the PA view of each study, in accordance with some embodiments of the present invention, (i.e., the approach described with reference to Rajpurkar, P., Irvin, J., Zhu, K., Yang, B., Mehta, H., Duan, T., Ding, D., Bagul, A., Langlotz, C., Shpanskaya, K., Lungren, M. P., Ng, A. Y.: *CheXNet: Radiologist-Level Pneumonia Detection on Chest X-Rays with Deep Learning.* (November 2017) and Wang, X., Peng, Y., Lu, L., Z.L.o.C.V., 2017, u.: *Chestx-ray8: Hospital-scale chest x-ray database and benchmarks on weakly-supervised classification and localization of common thorax diseases.* openaccess.thecvf.com). The numbers of the labeled dots depicted on the graph corresponding to the numbering of the possible visual findings presented in the table described with reference to FIG. 7. It is noted that for vertebral height loss, consolidation, rib fracture, and kyphosis, the lateral view which was processed by the trained classifier described herein in addition to the PA view resulted in improved detection rates in comparison to PA view alone. The results depicted by the graph indicate that the classifier trained here according to two or more anatomical image that each depict a certain unique orientation of the patient achieve improved detection accuracy in comparison to methods that are based on a single anatomical image depicting one patient orientation.

Reference is now made to FIG. 12, which is a table presenting results of a variant of the classifier described herein trained only with one anatomical image (i.e., PA view) for comparison with the classifier described herein trained with two anatomical images (i.e., denoted base, trained using PA and lateral views), as described with reference to the experiment. The label FC denotes the variant of the classifier trained with the fully-covered training set. The performance of the variant is shown for each of the 40 visual findings, measured in AUC. However, the variant achieved significantly lower results in almost all visual findings, suggesting that the additional abnormal studies in the any-hit set, more than compensated for the higher label noise.

Figure 13:
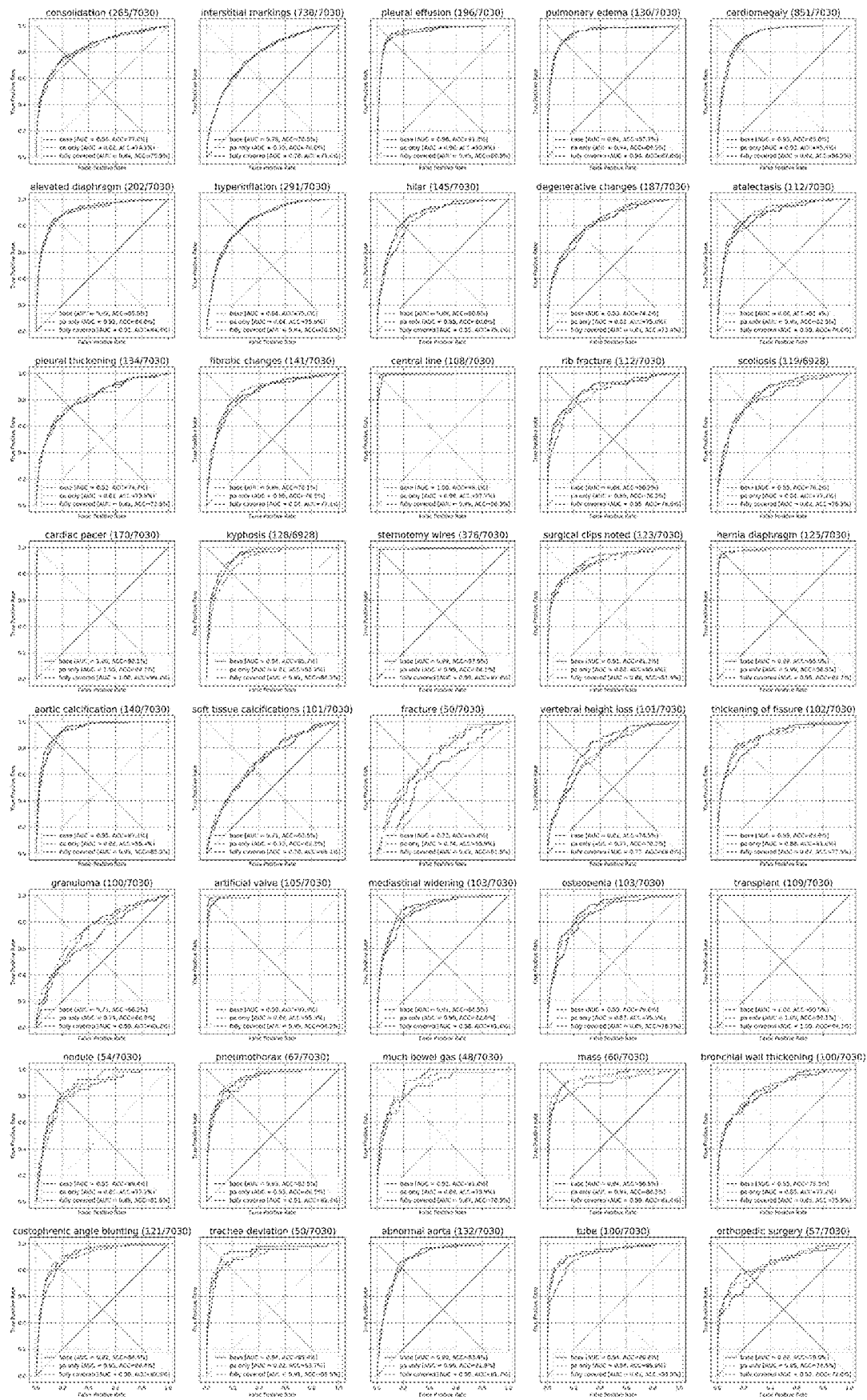
FIG. 13 includes images of heat maps computed according to the results of the classifier used in the experiment, in accordance with some embodiments of the present invention.

Reference is now made to FIG. 13, which includes images of heat maps computed according to the results, in accordance with some embodiments of the present invention. The heat maps presented in FIG. 13 were computed based on the procedure described with reference to Wang, X., Peng, Y., Lu, L., Z.L.o.C.V., 2017, u.: *Chestx-ray8: Hospital-scale chest x-ray database and benchmarks on weakly-supervised classification and localization of common thorax diseases.* openaccess.thecvf.com. Heat maps are presented for 12 of the positive findings described with reference to the experiment. Heat maps are presented over selected lateral and PA images. One heat map 1302 is marked, where heat map 1302 depicts a cardiac pacer on a PA view chest x-ray 1304.

Reference is now made to FIG. 14, which is a table presenting the most frequent positive sentences and corresponding number of occurrences in the set of radiology reports used in the experiment, in accordance with some embodiments of the present invention.

Figure 15:
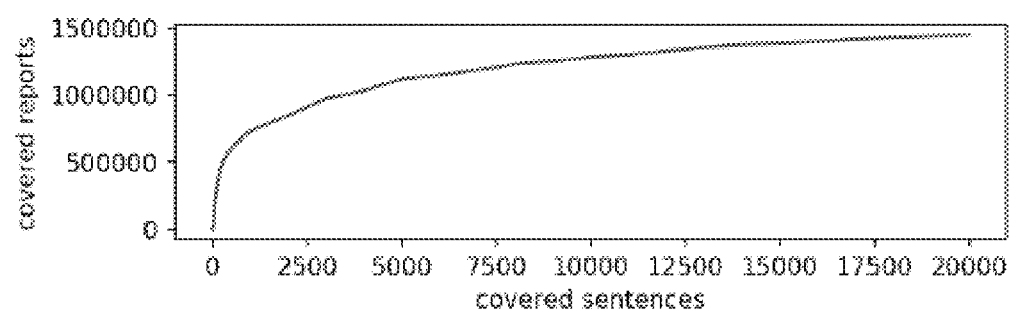
FIG. 15 is a graph presenting the number of radiology reports used in the experiment that are fully covered by sentences mapped to a certain visual finding as a function of the number of mapped sentences, in accordance with some embodiments of the present invention.

Reference is now made to FIG. 15, which is a graph presenting the number of radiology reports used in the experiment that are fully covered by sentences mapped to a certain visual finding as a function of the number of mapped sentences, in accordance with some embodiments of the present invention. The graph is generated based on the assumption that the most common sentences are mapped.

Reference is now made to FIG. 16, which is a table presenting agreement rates of assigned manual radiology taggers (marked as A-G) for different visual findings, as described with reference to the experiment. The taggers A-G are attending radiologists with 40, 6, 5, 5, 2, 2, and 2 years of experience, respectively. The numbers indicate the average agreement rate (AAR) of each radiologist versus the other two radiologists in the set.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

It is expected that during the life of a patent maturing from this application many relevant anatomical images will be developed and the scope of the term anatomical image is intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A computer implemented method for identification of an indication of at least one of a plurality of visual findings in at least one of two anatomical images of a target individual, comprising:
   providing two anatomical two dimensional (2D) images of a body portion of a target individual, each of the two anatomical 2D images captured at a unique orientation of at least the body portion of the target individual;
   inputting a first anatomical 2D image of the two anatomical 2D images captured at a first unique orientation into a first processing path comprising a first convolutional neural network (CNN) component of a statistical classifier to output a first feature vector;
   inputting a second anatomical image 2D of the two anatomical 2D images captured at a second unique orientation into a second processing path comprising a second CNN component of the statistical classifier to output a second feature vector;
   concatenating the first feature vector outputted by the first processing path and the second feature vector outputted by the second processing path;
   inputting the concatenation of the first feature vector and the second feature vector into a combined processing path comprising a fully connected layer component of the statistical classifier; and
   computing an indication of at least one of a plurality of distinct visual findings present in at least one of the two anatomical 2D images by the fully connected layer,
   wherein the statistical classifier is trained on a training dataset including, for each of a plurality of sample individuals, two anatomical 2D images of a body portion of the respective sample individual each captured at a respective unique orientation of at least the body portion of the target individual, and a tag associated with the two anatomical images, wherein the tag is created based on an analysis that maps respective individual sentences of a text based radiology report to one of a plurality of indications of visual findings.

2. The method of claim 1, wherein the two anatomical images depict non-parallel viewing planes of the patient from the anatomical imaging sensor.

3. The method of claim 1, wherein each one of the plurality of indications of distinct visual findings is based on one of a plurality of clusters created by clustering a plurality of sentences from respective text based radiology reports of a plurality of sample individuals.

4. The method of claim 1, wherein the anatomical imaging device comprises an x-ray machine that captures a two dimensional anatomical image.

5. The method of claim 1, wherein the anatomical imaging device comprises a mammography machine that captures a two dimensional anatomical images of two views per breast, including a mediolateral oblique (MLO) view and a craniocaudal (CC) view.

6. The method of claim 1, wherein a first anatomical image is captured when the target individual is oriented laterally relative to an anatomical imaging device, and a second anatomical image is captured when the target individual is oriented anterior-posterior (AP) or posterior-anterior (PA) relative to the anatomical imaging device.

7. The method of claim 1, wherein a first anatomical image is captured when the target individual is oriented supine relative to an anatomical imaging device, and a second anatomical image is captured when the target individual is oriented upright relative to the anatomical imaging device.

8. The method of claim 1, wherein the body portion of the target individual comprises at least one of: a chest, an abdomen, and a limb of the target individual.

9. The method of claim 1, wherein the classifier computers the indication of at least two visual findings in at least one of the two anatomical images by the fully connected layer.

10. The method of claim 1, wherein the plurality of visual findings include at least two members selected from the group consisting of: abnormal aorta, aortic calcification, artificial valve, atelectasis, bronchial wall thickening, cardiac pacer, cardiomegaly, central line, consolidation, costrophenic angle blunting, degenerative changes, elevated diaphragm, fracture, granuloma, hernia diaphragm, hilar prominence, hyperinflation, interstitial markings, kyphosis, mass, mediastinal widening, much bowel gas, nodule, orthopedic surgery, osteopenia, pleural effusion, pleural thickening, pneumothorax, pulmonary edema, rib fracture, scoliosis, soft tissue calcification, sternotomy wires, surgical clip noted, thickening of fissure, trachea deviation, transplant, tube, and vertebral height loss.

11. The method of claim 1, wherein the plurality of visual findings include at least two members selected from the group consisting of: masses, calcifications, calcified masses, calcification clusters, distortions, asymmetries, densities and scars.

12. The method of claim 1, further comprising computing by the statistical classifier, a confidence score indicative of a probability of the presence of each of the plurality of visual findings in at least one of the two anatomical images.

13. The method of claim 12, further comprising computing a heat map according to the confidence score for each of the plurality of visual findings, and presenting the heat map as an overlay of at least one of the two anatomical images.

14. A method of training a statistical classifier for identification of at least one of a plurality of visual findings in at least one of two anatomical images of a target individual, comprising:
   providing, for each of a plurality of sample individuals, two anatomical 2D images of a body portion of the respective sample individual each captured at a respective unique orientation of at least the body portion of the target individual, and a text based radiology report including a plurality of sentences;

creating, for each of the plurality of sample individuals, a respective tag according to an analysis that maps at least one of the plurality of sentences to a respective certain indication of a plurality of indications of distinct visual findings present in at least one of the two anatomical 2D images of the respective individual; and training a statistical classifier for identification of at least one of a plurality of visual findings in at least one of two anatomical 2D images of the body portion of a target individual according to a training dataset comprising the respective two anatomical images and respective tag for each of the plurality of sample individual, wherein the statistical classifier includes a first processing path comprising a first CNN component that outputs a first feature vector when fed a first anatomical 2D image captured at a first unique orientation, a second processing path comprising a second CNN component that outputs a second feature vector when fed a second anatomical 2D image captured at a second unique orientation, the first feature vector outputted by the first processing path and the second feature vector outputted by the second processing path are concatenated and fed into a combined processing path comprising a fully connected layer component of the statistical classifier that outputs the indication of at least one of the plurality of visual findings in at least one of two anatomical 2D images.

15. The method of claim 14, further comprising clustering the plurality of sentences from the respective text based radiology report of the plurality of sample individuals into a plurality of clusters, wherein each one of the plurality of indications of distinct visual findings is based on one of the plurality of clusters.

16. The method of claim 14, wherein the statistical classifier includes a first CNN that computes a first feature vector according to an inputted first anatomical image of the two anatomical images, a second CNN designed to output a second feature vector according to an inputted second anatomical image of the two anatomical images, and a fully connected layer that outputs an indication of at least one of a plurality of visual findings according to a concatenation of the first feature vector and the second feature vector.

17. The method of claim 14, wherein for each text based radiology report of each of the plurality of sample individuals, a sub-set of the plurality of sentences of the respective text based radiology report indicative of positive findings are mapped to the one of the plurality of indications of visual findings, and another sub-set of the plurality of sentences indicative of at least one of negative findings, neutral data, and ambiguous data is indicative of no visual findings and not mapped to one of the plurality of indications of visual findings.

18. The method of claim 14, further comprising creating a fully covered training dataset according to a sub-set of the text based radiology reports of the plurality of sample individuals, where for respective text based radiology report of each of the sub-set of the text based radiology reports, each one of the sentences of the respective text based radiology report is mapped to one of: one of the plurality of indications of visual findings, a negative finding, and neutral data, wherein the classifier is trained according to the fully covered training dataset.

19. The method of claim 14, further comprising creating an any hit training dataset according to a sub-set of the text based radiology reports of the plurality of sample individuals, where for respective text based radiology report of each of the sub-set of the text based radiology reports, at least one of the sentences of the respective text based radiology report is mapped to one of the plurality of indications of visual findings, wherein the classifier is trained according to the any hit training dataset.

20. The method of claim 14, wherein the statistical classifier is trained according to a main loss function based on a mean of binary cross-entropy losses.

21. A system for identification of an indication of at least one of a plurality of visual findings in at least one of two anatomical images of a target individual, comprising:
a non-transitory memory having stored thereon a code for execution by at least one hardware processor, the code comprising:
code for providing two anatomical 2D images of a body portion of a target individual, each of the two anatomical 2D images captured at a unique orientation of at least the body portion of the target individual;
code for inputting a first anatomical 2D image of the two anatomical 2D images captured at a first unique orientation into a first processing path comprising a first convolutional neural network (CNN) component of a statistical classifier to output a first feature vector;
code for inputting a second anatomical image 2D of the two anatomical 2D images captured at a second unique orientation into a second processing path comprising a second CNN component of the statistical classifier to output a second feature vector;
code for concatenating the first feature vector outputted by the first processing path and the second feature vector outputted by the second processing path;
code for inputting the concatenation of the first feature vector and the second feature vector into a combined processing path comprising a fully connected layer component of the statistical classifier; and
code for computing an indication of at least one of a plurality of distinct visual findings present in at least one of the two anatomical 2D images by the fully connected layer,
wherein the statistical classifier is trained on a training dataset including, for each of a plurality of sample individuals, two anatomical 2D images of a body portion of the respective sample individual each captured at a respective unique orientation of at least the body portion of the target individual, and a tag associated with the two anatomical images, wherein the tag is created based on an analysis that maps respective individual sentences of a text based radiology report to one of a plurality of indications of visual findings.

22. The system of claim 21, further comprising code for training a statistical classifier for identification of at least one of a plurality of visual findings in at least one of two anatomical images of a target individual, comprising:
code for providing, for each of a plurality of sample individuals, two anatomical images of a body portion of the respective sample individual each captured at a respective unique orientation of at least the body portion of the target individual, and a text based radiology report including a plurality of sentences;
code for creating, for each of the plurality of sample individuals, a respective tag according to an analysis that maps at least one of the plurality of sentences to a respective certain indication of a plurality of indications of distinct visual findings present in at least one of the two anatomical images of the respective individual; and code for training a statistical classifier for identification of at least one of a plurality of visual findings in at least one of two anatomical images of the body portion of a target individual according to a training dataset comprising the respective two anatomical images and respective tag for each of the plurality of sample individual.

* * * * *